(12) United States Patent
Norman

(10) Patent No.: US 7,829,326 B2
(45) Date of Patent: Nov. 9, 2010

(54) ENCODED CARRIER

(75) Inventor: Carl Edward Norman, Cambridge (GB)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/915,323

(22) Filed: Aug. 11, 2004

(65) Prior Publication Data

US 2005/0079635 A1     Apr. 14, 2005

(30) Foreign Application Priority Data

Aug. 11, 2003  (GB) ................................. 0318808.3
Aug. 6, 2004   (GB) ................................. 0417591.5

(51) Int. Cl.
    G01N 33/553    (2006.01)
(52) U.S. Cl. ....................... 435/287.1; 385/12; 385/129; 385/130; 422/82.11; 435/288.7; 435/808; 436/524; 436/525; 436/805
(58) Field of Classification Search ................. 356/517; 422/58, 82.05; 435/7.1, 28.31, 287.9; 977/773, 977/774, 918
See application file for complete search history.

(56) References Cited

U.S. PATENT DOCUMENTS

| 5,846,843 | A | * | 12/1998 | Simon | .................. 436/527 |
|---|---|---|---|---|---|
| 5,955,378 | A | | 9/1999 | Challener | |
| 5,976,895 | A | * | 11/1999 | Cipkowski | .................. 436/518 |
| 6,017,696 | A | * | 1/2000 | Heller | ............................ 435/6 |
| 6,432,364 | B1 | * | 8/2002 | Negami et al. | ............ 422/82.11 |
| 6,838,051 | B2 | * | 1/2005 | Marquiss et al. | ............... 422/63 |
| 7,070,987 | B2 | * | 7/2006 | Cunningham et al. | ..... 435/287.1 |
| 2003/0017580 | A1 | | 1/2003 | Cunningham et al. | |

FOREIGN PATENT DOCUMENTS

| JP | 2002-357543 | 12/2002 |
|---|---|---|
| JP | 2003-75337 | 3/2003 |
| JP | 2003-121350 | 4/2003 |
| WO | WO 00/01475 | 1/2000 |
| WO | WO 00/16893 | 3/2000 |
| WO | WO 00/63419 A1 | 10/2000 |
| WO | WO 01/62699 A1 | 8/2001 |

* cited by examiner

*Primary Examiner*—Christopher L Chin
(74) *Attorney, Agent, or Firm*—Oblon, Spivak, McClelland, Maier & Neustadt, L.L.P.

(57) ABSTRACT

An encoded carrier includes a code region having a code, and a reaction region separate from the coded region, the reaction region having a variation in its refractive index or dielectric constant in a direction generally parallel to the surface of the reaction region.

22 Claims, 23 Drawing Sheets

ENCODED CARRIER

The present invention relates to the field of encoded carriers primarily for use in analysing a particular chemical species or to monitoring molecular reactions.

There has always been a need to be able to quickly and efficiently monitor reactions between different chemicals in order to both identify unknown molecules and to study the reactions of both known and unknown molecules. This need has become all the more acute with the substantial and numerous discoveries being made in the biotechnology field.

DNA has the capacity to "hybridise", in other words, a single strand of DNA is capable of pairing to its complementary single strand but not pairing to an unrelated sequence. Using this technique it is possible to identify and monitor the reactions of an unknown strand of DNA by attempting to hybridise it with known DNA strands.

Currently, there are a number of methods for performing this analysis. In one of the known methods, a known molecule or "probe" is reacted with an unknown molecule or "target", to analyse the target molecule. The probe is tethered to a stable material and is generally labelled with a radioactive isotope or fluorophore that can be detected after hybridisation takes place.

WO00/16893 describes a system where probes are attached to a plurality of different coded carriers. The target molecules are tagged and are introduced to the probes with the coded carriers.

GBP2306484 relates to a technique similar to WO00/16893 which uses coded carriers in order to monitor reactions between polymers and the like.

In a further method, a so-called DNA microarray, "spots" of different probe molecules are attached to an inert material such as glass or nylon which are then exposed to labelled target molecules.

Although effective, the above methods are label or tag based methods which require the awkward process of attaching a fluorescent tag molecule to either the probe or the target molecule which can be difficult and time consuming to implement. Interest is now growing in non-tag based methods One envisaged method uses surface plasmon resonance to determine whether or not a reaction has taken place between a probe located in a microarray and a target, see for example, Brockman et al, "Grating Coupled Surface Plasmon Resonance for Rapid Label-Free, Array-based sensing", American Laboratory, June 2001, Pages 37 to 40.

In the above method, the probes are attached to a gold layer which is provided on a plastic optical grating. On performing a surface plasmon resonance measurement, light is reflected off the gold layer to excite the metal surface plasmon at the gold/dielectric interface. When light is incident on the grating at a particular angle, light couples to the surface plasmon causing a resonance condition where more of the light is absorbed by the structure causing a decrease of the amplitude of the reflected light. The grating serves to couple radiation with the correct incident angle and properties to the surface plasmon mode.

The above proposed surface plasmon resonance technique still has its drawbacks in that it is difficult to test a large number of different molecules at any one time.

The present invention attempts to address the above problems and in a first aspect provides an encoded carrier comprising a code region having a code and a reaction region separate from said code region, said reaction region having a variation in its refractive index or dielectric constant in a direction generally parallel to the surface of the reaction region.

The variation in the refractive index of the reaction region allows the presence or absence of molecules on the surface of the reaction region to be investigated using a range of techniques. The variation may be a periodic modulation or a non-periodic variation.

In practice, a plurality of known molecules or "probes" will be attached to the reaction region of the encoded carrier. A physical property of the reaction region, will then be measured with the probes attached to the reaction region. Examples of physical properties which may be measured is the reflectance or transmission of the reaction region.

The encoded carriers with probes will then be introduced to molecules of a second type or "targets". Depending on the types of molecules used for the probe and the target, a reaction may take place. For example, if the target is a stand of DNA and the probe is a complementary strand of DNA then hybridisation will occur. If the target is a strand of DNA and the probe is a strand of DNA with a sequence unrelated to that of the target then no hybridisation will occur. If a reaction, such as hybridisation takes place, the measured physical property of the reaction region will change, hence it is possible to determine if the reaction has happened.

Attaching probes to the reaction region is a relatively easy process and may be achieved by placing an encoded carrier with a suitable surface into a solution of probes or they may be "spotted" onto the surface of the reaction region. Suitable materials for the reaction region will be discussed later.

Typically, a number of different encoded carriers will be used, each with a different probe. Carriers with different probes will have different codes, so that each probe may be identified by reading the code on the carrier. Thus, different probes may be reacted at once with a target molecule. To determine which of the different probes have reacted with the target, the physical properties of a number of the encoded carriers will be measured, then the codes on the encoded carriers which have reacted will be read to determine exactly which probes reacted with the target.

The above system allows thousands and possibly millions of different probes to be reacted with a target in one experiment, since the different probes may be easily distinguished from one another due to their unique code.

In a preferred embodiment, the reaction region is configured to support surface plasmons and said variation in the refractive index or dielectric constant is configured to couple incident radiation to surface plasmons excited by said radiation.

If radiation is incident on the reaction region at a particular angle, the "resonance angle", the incident radiation couples to the surface plasmons and there is a drop in the reflectance of the reaction region at this angle. The resonance angle is determined by a number of factors such as the wavelength of the incident radiation and the composition of the reaction region and general shape and surface topography of the reaction region. Thus, the resonance angle will vary depending on the molecules (e.g. probe and target molecules) which are attached to the surface of the reaction region.

For this embodiment, the variation in the refractive index or dielectric constant is a periodic variation or a modulation. The modulation in the refractive index or dielectric constant is provided by a diffraction grating. The diffraction grating may be one dimensional or two dimensional. Preferably, the diffraction grating should be a first order or second order diffraction grating.

As previously described, the resonance angle is determined by, in addition to the wavelength of the incident radiation and the composition of the reaction region, the surface topography of the reaction region. Thus, changes in the grating period, pitch and general shape can affect the resonance angle.

The grating may be a planar grating comprising a plurality of regularly spaced holes which extend through the whole of the reaction region or indents and/or ridges which do not pierce the whole of the reaction region. The holes or indents may be elongated to form a ID diffraction grating or may be generally symmetric to from a 2D diffraction grating.

The diffraction grating may also comprise a corrugated structure.

When studying how reflected radiation is affected by the radiation coupling to surface plasmons, the reaction region preferably comprises a dielectric layer and a metal layer.

The metal layer may be selected from Al, Au, Cr, Co, Cu, In, Fe, Pb, Mg, Mn, Mo, Ni, nichrome, Nb, Pd, Pt, Se, Ag, Ta, Te, Sn, Ti, W, Zn, and Zr.

The dielectric layer may be selected from $Al_2O_3$, $BaTiO_3$, CdO, CdSe, CdS, $CeO_2$, Germanium oxide, indium oxide, $Fe_2O_3$, $Fe_3O_4$, $MgF_2$, $SiO_2$, SiO, $Si_3N_4$, tin oxide, $TiO_2$, TiO, ZnSe, and ZnS.

Diffraction gratings may also rotate the polarisation of reflected radiation, the degree of rotation is affected by coatings on the surface of the reaction region and can thus be used to determine the presence of target molecules.

To study changes in the polarisation of the incident radiation, the diffraction grating is preferably a zero order grating.

The variation in the refractive index or dielectric constant may alternatively be provided by a plurality of holes which extend through the whole of said reaction region. The holes may or may not be in a regular array. In this type of structure, probe molecules are attached to the inside of the holes and target molecules may attach themselves to the probe molecules. Radiation incident on the reaction region will be transmitted through the holes. However, depending on the conditions of the incident radiation and the composition of the walls of the holes, surface plasmons may be excited within the walls of the holes at the boundary between the hole and the probe molecules. These surface plasmons will "carry" radiation through the carrier and hence increase the amount of radiation transmitted through the carrier. Thus, the amplitude of the transmitted radiation may be affected by the presence of target molecules and this may be used to check for the presence of target molecules.

When checking for the presence of target molecules by measuring changes in the amplitude of transmitted radiation or by measuring changes in the polarisation of reflected radiation, the reaction region preferably comprises a metal layer. The metal layer may be any of those described above.

The reaction region may be single sided where the reaction region is planar and the reaction region may only be measured on one side. Alternatively, the reaction region may be two sided such that it may be measured on either side.

Conveniently, for carriers where surface plasmons are used to determine the presence or absence of target molecules and the reaction region is two sided, the carrier may be provided with probe molecules on one side only such that the carrier can distinguish between the presence of target molecules and external factors such as wholesale changes in the refractive index of the surrounding medium thermal or vibrational effects. For carriers configured in such a manner the presence of target molecules will affect surface plasmon activity only on the side of the carrier provided with the probe molecules. If surface plasmon resonances are affected on both sides then this would be indicative of factors other than the presence of target molecules, be they changes in the overall refractive index of the surrounding medium, system temperature or vibrational effects. In such a case, measuring the plasmon resonance shift on both sides of the carrier will allow a differential measurement to be made, thereby allowing resonance shifts due to target molecules to be separately identified.

Where there is a metal and dielectric layer, which layer is uppermost will mainly be dictated by the bonding characteristics of the probe molecules.

Where surface plasmons are used to determine the presence or absence of target molecules, the interface where the plasmons are generated should be close enough to the probe and target molecules such that the presence of target molecules affects the surface plasmons. Typically, the site at which the target molecules should attach is within 50 nm of the interface where the surface plasmons are generated.

The code located in the code region may be a code such as an alphanumeric code or a barcode. In general, any geometric code may be used.

The carrier may be generally planar and the code may be provided at or close to two or more edges of said carrier.

Preferably said carrier is generally planar and said code is configured such that it can be uniquely identified regardless of which plane of the carrier is uppermost.

The code may extend through the whole of the width of said carrier and is preferably provided at the edge of the carrier where each character of the code is fully open to the edge of the carrier.

Preferably, the encoded carrier is less than 400 µm by 400 µm, more preferably less than 100 µm by 100 µm.

In a second aspect, the present invention provides a method of tracking a chemical reaction between probe molecules of a first type and target molecules of a second type, the method comprising:
attaching probe molecules to an encoded carrier, said encoded carrier comprising a code region having a code and a reaction region separate from said code region, said reaction region having a variation in its refractive index or dielectric constant in a direction generally parallel to the surface of the reaction region;
introducing the encoded carriers with probe molecules to target molecules; and
measuring a physical property of the reaction region to determine if the probe molecules have reacted with the target molecules.

The above method may be extended to a plurality of probes, where:
a plurality of different types of probe molecules are attached to the reaction region of a plurality of encoded carriers having different codes, such that each type of probe molecule is attached to carriers having the same code;
the plurality of encoded carriers with different codes and probe molecules are introduced to target molecules;
a physical property of the reaction region for each carrier is measured and its code is read to determine which of the probe molecules have reacted with the target molecules.

As previously explained measuring a physical property of the reaction region may comprise measuring the reflectance of the reaction region or the transmittance of the reaction region.

The reflectance may be measured as a function of the angle of incidence of radiation reflected from the reaction region, as a function of the wavelength of the reflected radiation or as a function of the polarisation of the reflected radiation.

The reaction kinetics may be monitored since the measured physical property of the reaction region will change dependent on the number of target molecules which have reacted with the probes. Thus, by measuring the physical property of the reaction region at different times after the probes have been mixed with the targets, it is possible to obtain information about the reaction kinetics.

In a third aspect, The present invention provides a method of fabricating an encoded carrier, said encoded carrier comprising a code region having a code and a reaction region separate from said code region, said reaction region having a variation in its refractive index or dielectric constant in a direction generally parallel to the surface of the reaction, said method comprising:

providing a substrate having a raised pattern formed on a surface of said substrate, said raised pattern comprising at least one material which forms said surface and defining a reaction area and a coded area having a code;

depositing material over said raised pattern; and dissolving said substrate to release said deposited material to form said encoded carrier from said released deposited material.

In a fourth aspect, the present invention provides an apparatus for reading an encoded carrier, said encoded carrier comprising a code region having a code and a reaction region separate from said code region, said reaction region having a variation in its refractive index or dielectric constant in a direction generally parallel to the surface of the reaction region, said apparatus comprising:

means to perform a measurement of a physical property of the reaction region; and means to read the code provided on said coding area.

The means to perform a measurement of a physical property may be configured to measure the amplitude of the reflected radiation as a function of angle of incidence of the radiation or as a function of the wavelength of the reflected radiation. Alternatively, the means to perform a measurement of a physical property may be configured to measure the amplitude of the reflected radiation at a predetermined polarisation or the amplitude of the transmitted radiation.

The terms "probe" or "probe molecules" have been used to refer to the molecules which are attached to the encoded carrier. The terms "target" or "target molecules" have been used to refer to the molecule which is to be reacted with the molecules already attached to the encoded carriers. The probes and targets may be chosen from a number of different types of molecules for example, antibodies, antigens, enzymes, toxins, proteins, genes etc.

The present invention will now be described with reference to the following non-limiting embodiments in which:

BRIEF DESCRIPTION OF THE DRAWINGS

FIG. 1a is a schematic of an encoded carrier in accordance with an embodiment of the present invention undergoing a surface plasmon resonance measurement prior to reaction of the encoded carrier with a target species, FIG. 1b is a plot of reflected amplitude against angle of incidence indicating the resonance angle;

Figure 1:
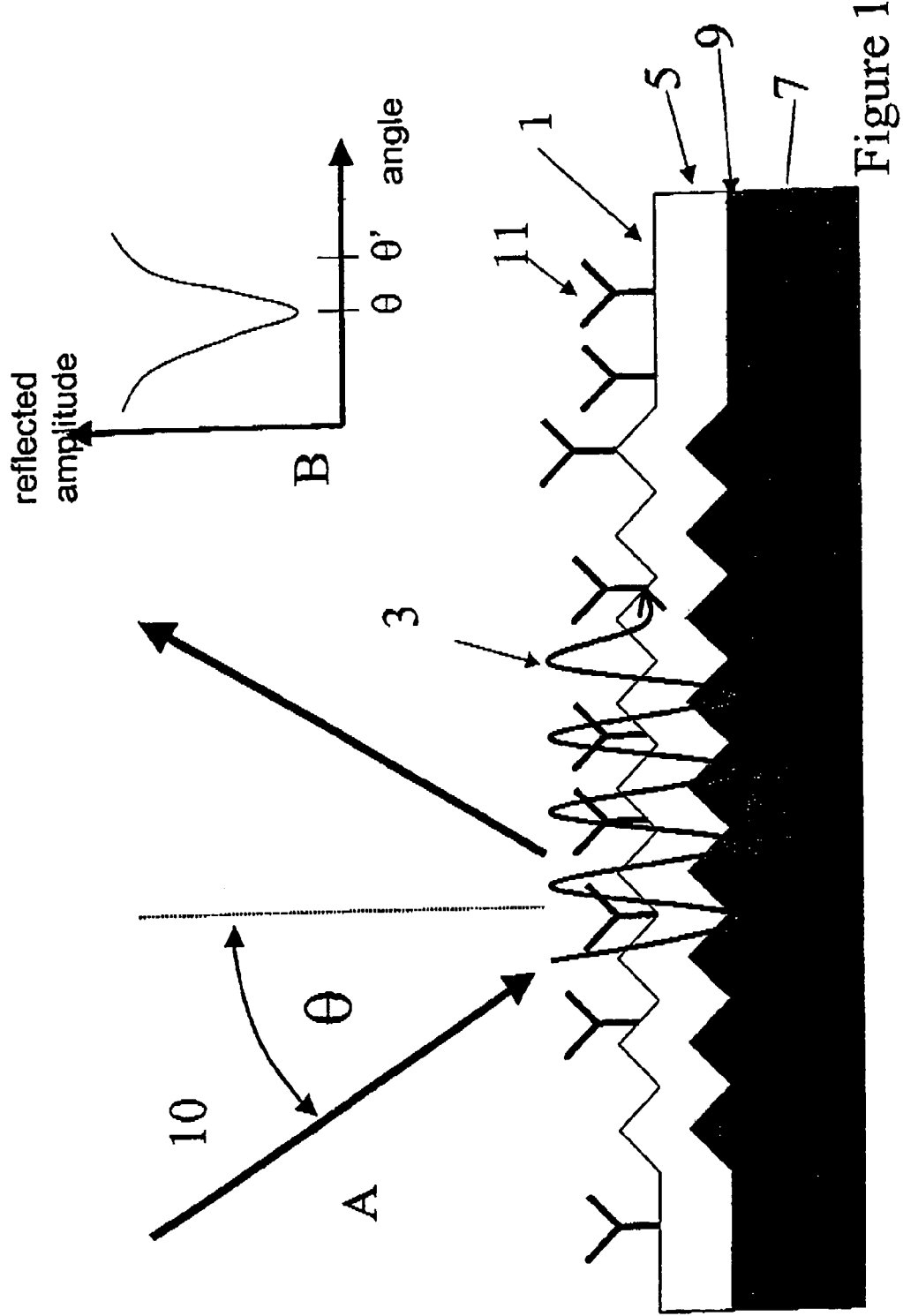
FIG. 1 a is a schematic cross-section of an encoded carrier 1. The encoded carrier 1 comprises a first dielectric layer 5 of $SiO_2$ and a second metal layer 7 of Au. The order of these two layers may be reversed.

Region 3 is the reaction region of the encoded carrier 1, in this region, the first dielectric layer 5 and second metal layer 7 are corrugated to form a diffraction grating.

A beam of radiation 10 is incident on said carrier 1 at angle θ. Radiation 10 enters the first layer 5 and the second layer 7. When the radiation has the appropriate wavelength, polarisation and angle of incidence, the energy from the incident radiation couples to the electrons of the metal layer 7 to excite surface plasmons at the interface 9 between the first dielectric layer 5 and the second metal layer 7. At this "resonance" condition, there is a steep fall in radiation reflected from the reaction region since this radiation is now absorbed by coupling to the surface plasmon mode.

The surface plasmon mode travels along the plane of the interface and extends for approximately 50 nm on either side of the interface 9. The characteristics of the surface plasmon mode can thus be governed by physical properties of layers which are within the range of the surface plasmon. Thus, providing that the interface is close enough to a surface of the reaction region, chemical species 11 adhering to the surface of the reaction region may affect the surface plasmon characteristics.

The present invention is primarily intended for determining if molecules of a first type or "probes", 11, react with molecules of a second type or "targets", 13.

In FIG. 2a, the probes 11 have adhered to the targets 13 and thus both chemical species are attached to metal layer 7, The presence of the targets 13 will further affect the angle at which incident radiation couples to the surface plasmons, or the "resonance angle".

In FIG. 1a, where just the probes 11 adhere to the surface of the reaction region, the resonance angle is θ to the surface normal. In FIG. 2b, where both the probes 11 and targets 13 adhere to the surface of the reaction region, the resonance angle is θ' to the surface normal. This is illustrated in FIGS. 1b and 2b respectively which show a plot of the reflected amplitude of radiation against the incident angle of radiation.

Thus, since the reaction between the probes 11 with the targets 13 causes a variation in resonance angle, measurement of the "resonance" angle, can be used to determine if the second type of molecules 13 has reacted to the first type of molecules 11.

Figure 2:
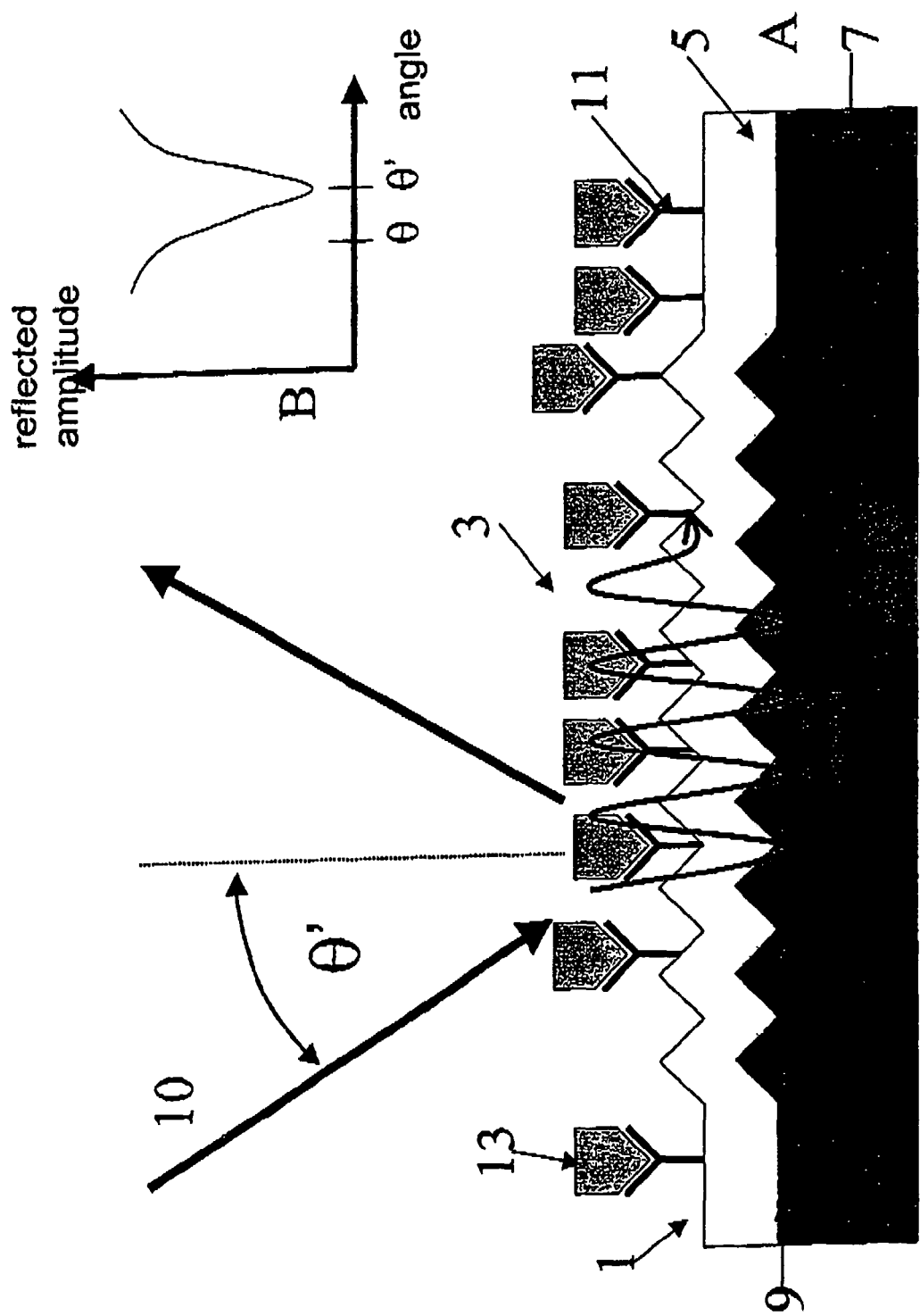
FIG. 2a is a schematic of the encoded carrier of FIG. 1a undergoing a surface plasmon resonance measurement after reaction of the encoded carrier with a target species.
FIG. 2b is a plot of reflected amplitude against angle of incidence indicating the resonance angle.
Figure 3:
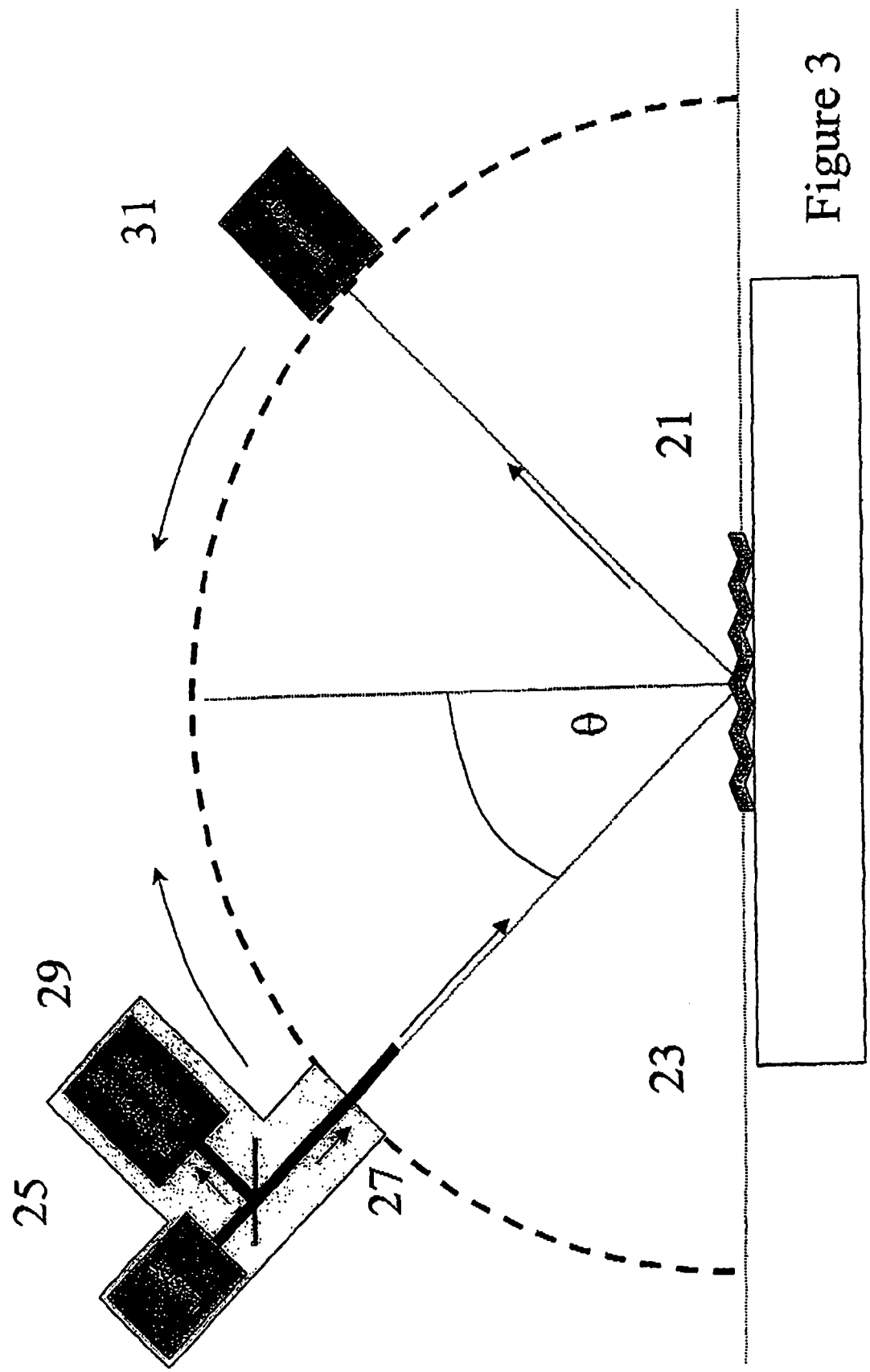
FIG. 3 is a schematic of a surface plasmon resonance measurement apparatus.

FIG. 3 schematically illustrates a measurement apparatus. Here, an encoded carrier 21 is provided on a substrate 23. The substrate 23 may be a glass or other type of substrate. The encoded carrier 21 may be the same encoded carrier described with reference to FIGS. 1a and 2a.

Laser 25 is rotatably mounted about a rotation axis which is roughly in the plane of the interface between the first and second layers of the encoded carrier 21 (the first and second layers are layers 5 and 7 respectively described with reference to FIGS. 1a and 2a). Laser 25 is rotatably mounted so that the angle of incidence θ, may be varied. Similarly, the detector 31 may be moved in order to detect the reflected radiation.

Laser 25 emits a beam of radiation which impinges on beam splitter 27. Beam splitter 27 sends part of the beam to a reference detector 29. Reference detector 29 ensures that the laser 25 is producing a known output. The remainder of the light is transmitted through beam splitter 27 and impinges on encoded carrier 21 at an angle θ to the surface normal. Light reflected from encoded carrier 21 is then reflected at an angle θ to the surface normal away from laser 25 and towards detector 31. Detector 31 is also rotatably mounted about a rotation axis which is roughly in the plain between the first and second layers of encoded carrier 21.

When the angle of incidence θ is such that the incident radiation couples to the surface plasmon mode, there is a sharp decrease in the amount of radiation reflected and thus detected by detector 31. As this angle θ is dependent on the chemical species attached to the surface of reaction region 3 (FIG. 1), it is possible to determine whether or not the probes have reacted with the targets.

Figure 4:
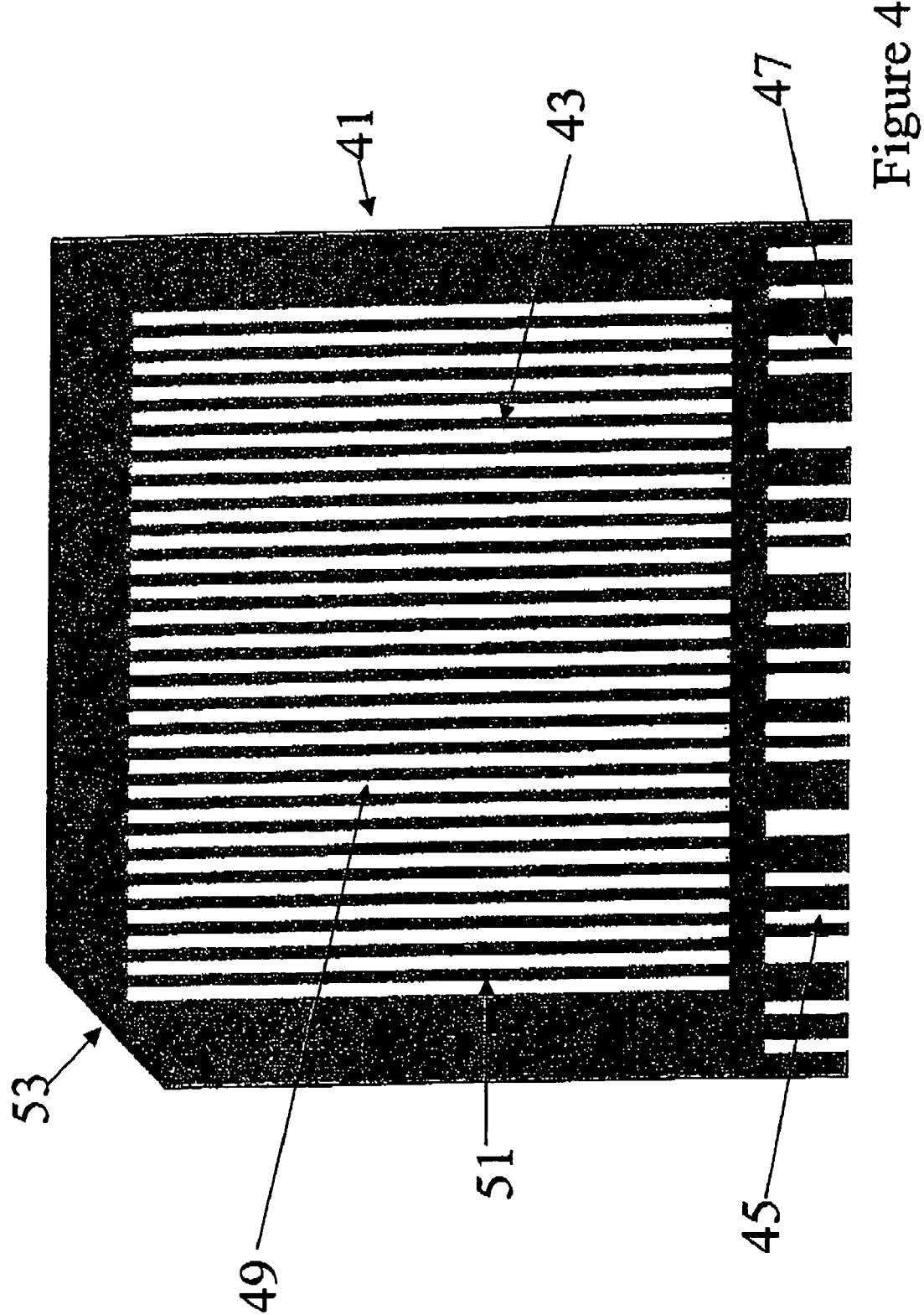
FIG. 4 is an encoded carrier having a planar striped diffraction grating and a bar code in accordance with an embodiment of the present invention.

FIG. 4 illustrates an encoded carrier in accordance with an embodiment of the present invention. The encoded carrier has a reaction region 43 and a coding region 45 comprising a code 47.

The reaction region 43 comprises a diffraction grating 49. In this embodiment, the diffraction grating comprises elongate rectangular holes 51 which are oriented parallel to one another and extend through the whole of the encoded carrier 41. Thus, the diffraction grating 49 comprises a plurality of stripes. Although in this particular embodiment, the holes 51 extend through the whole of the encoded carrier, they may also extend just part of the way into the reaction region, such that the diffraction grating 49 comprises alternating stripes of different thickness in the direction into the plane of the encoded carrier 41.

The code 47 is a bar code provided at the edge of the encoded carrier 41 and extends over the edge of the carrier 41. The advantage of extending the code over the edge of the carrier will be described with reference to FIG. 16. The code has been designed so that if the encoded carrier 41 is read from the opposite side, i.e. from underneath the plain of paper, each numeral can still be uniquely identified.

Corner 53 of encoded carrier 41 has been removed so that the orientation of the carrier can be determined. Confirmation of the orientation of the carrier 41 is necessary in order to correctly measure the reaction area since the orientation of the diffraction grating 49 with respect to the laser should be the same for all encoded carriers 41. The orientation of the carrier 41 may also be useful for reading the code 47.

Typically, the encoded carrier 41 will be 50 to 100 μm square. Each of the characters of the bar code will typically have a length between 5 and 10 μm.

In use, probes will be attached to reaction region 43. The molecules may be attached using a number of methods, but will preferably be attached by placing the encoded carriers in a solution of probes.

The encoded carriers 41 will then be introduced to molecules of a different type, "target molecules". Typically, this will again be performed by placing the encoded carriers with the probes in a solution or suspension of the target molecules.

If the probes attached to reaction area 43 react with the targets, the surface plasmon resonance characteristics of the reaction area will change as described with reference to FIGS. 1 to 3.

In practice, a plurality of encoded carriers 41 will be prepared, by attaching a first type of probes to a first plurality of encoded carriers having the same "first" code, a second type of probes (different to the first type of probes) to a second plurality of encoded carriers having the same "second" code. The second code is different to the first code. Further encoded carriers with third, fourth, fifth etc codes and types of probes will be prepared. The reaction region 43 for each different type of encoded carrier having a different probe will be analysed as explained with reference to FIG. 3 to determine the "resonance angle" prior to reaction.

The different types of encoded carriers 41 will then be introduced into a solution containing the target molecules. The encoded carriers may then be removed from the solution and measured. Alternatively, the carriers may be read while in the solution. Each type of encoded carrier may be determined from its code. An SPR measurement can then be performed to determine if the probes on the carrier have reacted with the target molecule.

The encoded carriers 41 may also be used to monitor the progress of a reaction between a molecule attached to the carrier and a target molecule. At the start of the reaction, only a few of the probes attached to the encoded carrier will react with target molecules. As the reaction progresses, more and more of the probes will react with the target molecules allowing the reaction kinetics to be studied.

Figure 5:
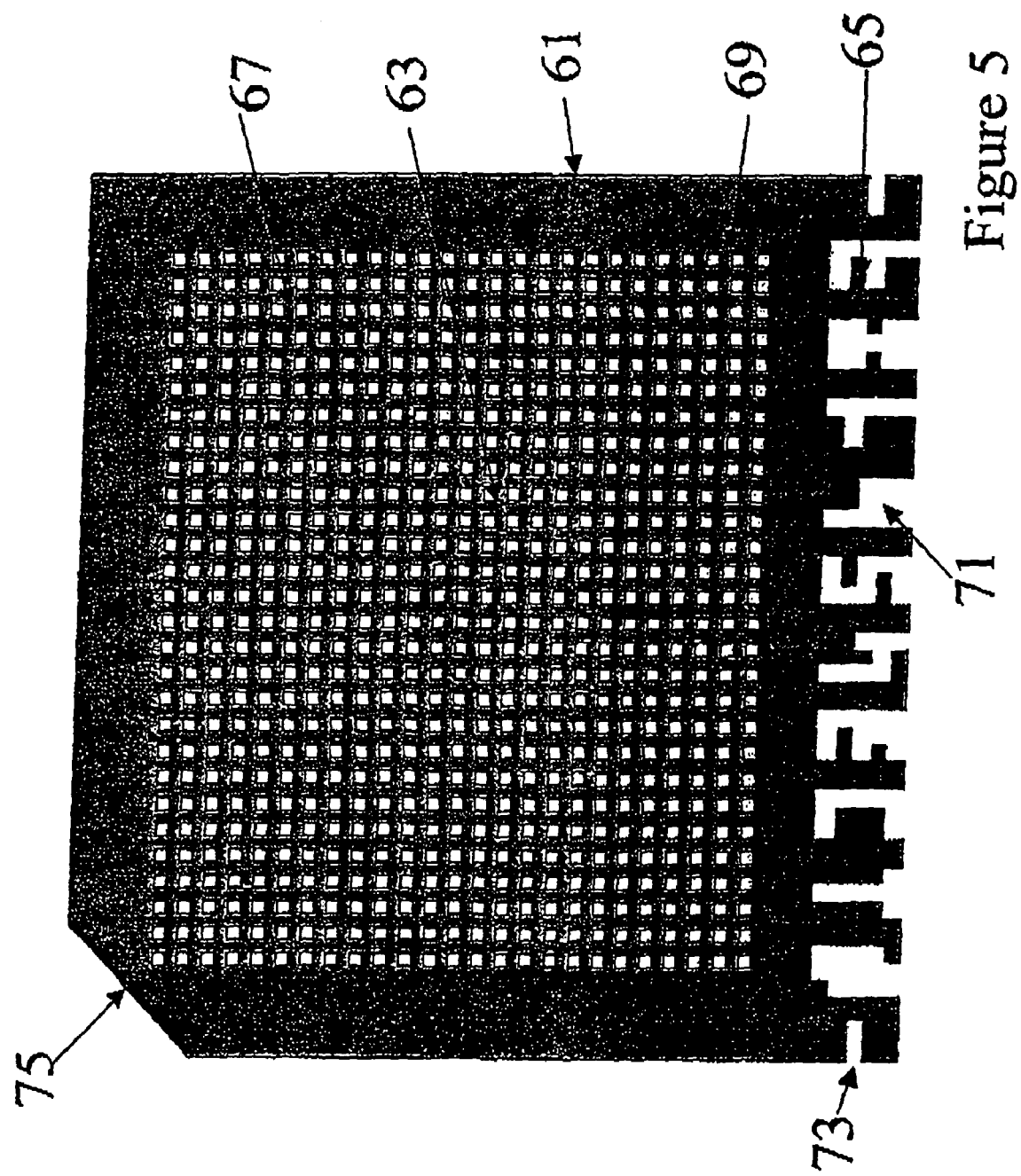
FIG. 5 is an encoded carrier having a planar grid-type diffraction grating and an alphanumeric code in accordance with a further embodiment of the present invention.

FIG. 5 schematically illustrates an encoded carrier 61. As for FIG. 4, the carrier 61 has a reaction region 63 and a code region 65.

The reaction region 63 comprises a diffraction grating 67. The diffraction grating 67 comprises a gird of holes 69 which extend through the whole of the encoded carrier 61. However, alternatively, the holes 69 may only extend part of the way through the encoded carrier to form a grid of indents.

The code region 65 comprises a code 71. The code 71 is an alphanumeric code which is designed so that each character can be uniquely identified regardless of whether the code 71 is read from above or below the plane of the encoded carrier 61. The code 71 is provided right at the edge of the carrier 61 and each character of the code is open to the edge of carrier 61. The reasons for this will be explained in detail with reference to FIG. 16 which explains the fabrication of the carrier. By forming the code at the edge of the carrier, there are no small pieces of debris which could become lodged in other characters of the code or at other positions on the carrier or there is a very small chance of a character not being fully formed.

Indents 73 are provided on either side of the code 71 and are used to indicate the central line of the code 71.

As in the carrier of FIG. 4, corner 75 has been removed to allow the orientation of the carrier 61 to be determined.

Figure 6:
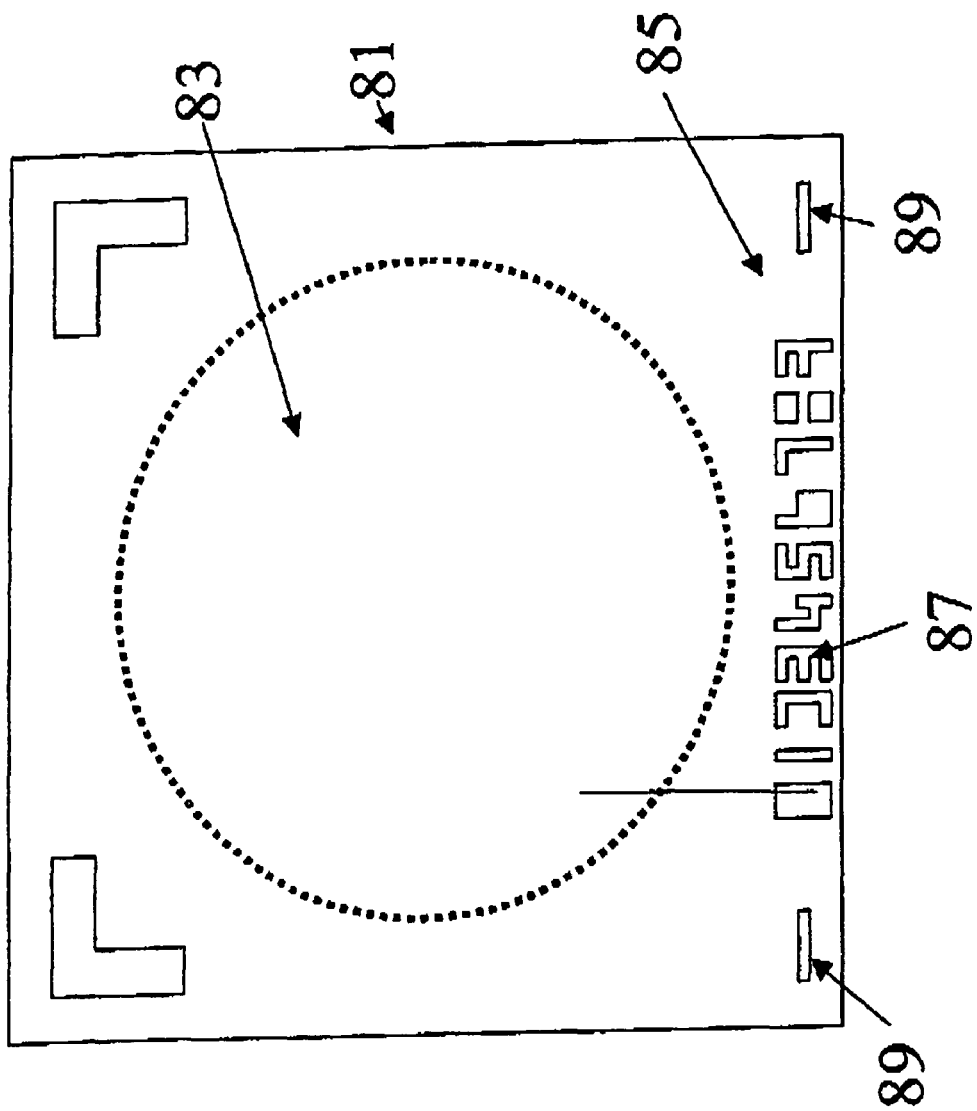
FIG. 6 is an encoded carrier in accordance with a further embodiment of the present invention having a an inset alphanumeric code.

FIG. 6 is a schematic of a further encoded carrier. The carrier 81 comprises a reaction region 83 and a code region 85. The reaction region 83 comprises a diffraction grating (not shown) which may be any of the types described previously with reference to FIGS. 4 and 5 or subsequently with reference to FIGS. 8 to 13.

The code region 85 comprises a code 87. The code 87 is an alphanumeric code which is readable from either side of the plane of the carrier 81. The code 87 is inset from the edge of the carrier 81 so that each character of the code is fully bounded. Elongate holes 89 are provided on either side of the code defining the middle line of the code.

Figure 7:
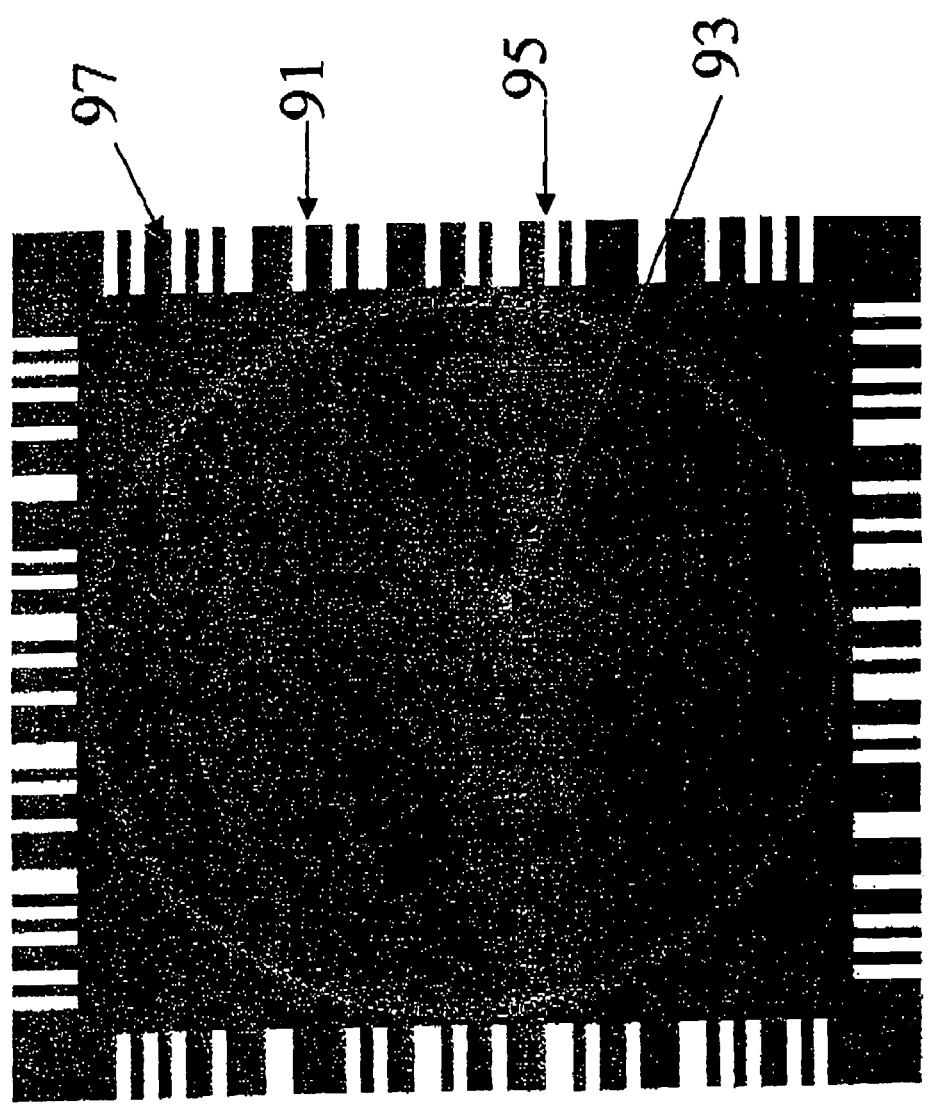
FIG. 7 is an encoded carrier in accordance with a further embodiment of the present invention having a bar code on all four sides.

FIG. 7 schematically illustrates a further type of encoded carrier 91. As for the other encoded carriers described with reference to FIGS. 4 to 6, the encoded carrier 91 comprises a reaction region 93 and a code region 95.

The reaction region 93 comprises a diffraction grating (not shown) which may be any of the types described previously with reference to FIGS. 4 and 5 or subsequently with reference to FIGS. 8 to 13.

In this particular embodiment, the reaction area 93 is the central region and the coding region 95 extends around the edge of the encoded carrier 91. Specifically, carrier 91 has a square shape and the code region 95 extends along all four sides of the square. A barcode 97 is provided on each side of the square. The same code is provided on each side of the square so that the carrier 91 may be placed in one of four orientations for the code to be read. The code must also be designed so that it can be uniquely determined regardless of whether the code is read from above or below the plane of the carrier 91.

Figure 8:
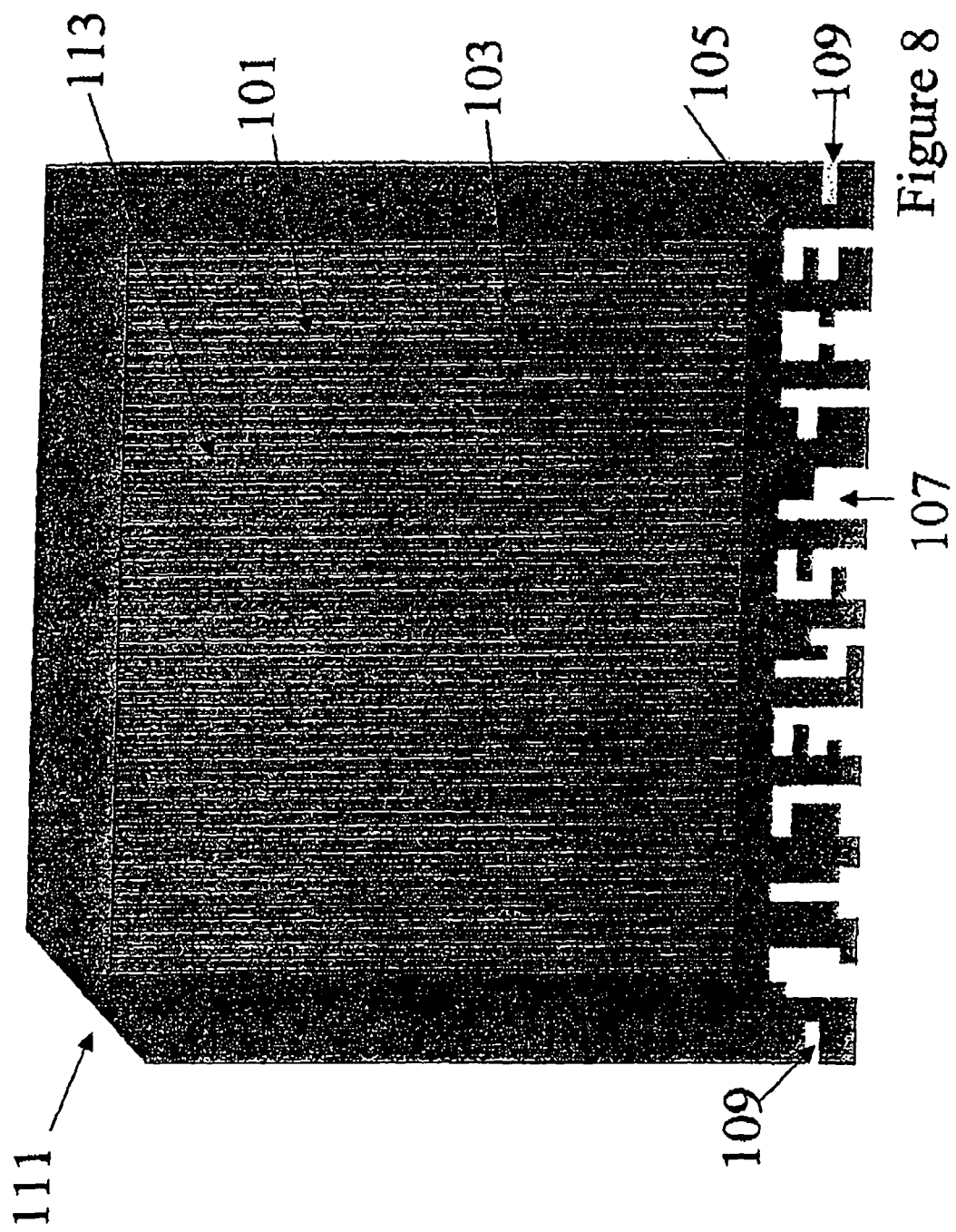
FIG. 8 is an encoded carrier having a corrugated diffraction grating and an alphanumeric code in accordance with a preferred embodiment of the present invention.

FIG. 8 shows a further type of encoded carrier 101. As for FIG. 4, the encoded carrier 101 has a reaction region 103 and a code region 105. A code 107 is provided on code region 105.

The code 107 is an alphanumeric code and each character is uniquely identifiable regardless of whether the code is read from above or below the plane of the carrier 101. Indents 109 are provided on either side of the code 107 indicating the middle line of the code 107.

As explained in relation to FIG. 4, corner 11 is missing to allow the orientation of the carrier 101 to be determined.

The reaction area 103 comprises a diffraction grating 113 formed from laminated corrugated layers. This diffraction grating allows incident radiation to couple to the surface plasmon as described with reference to FIGS. 1 and 2.

Figure 9:
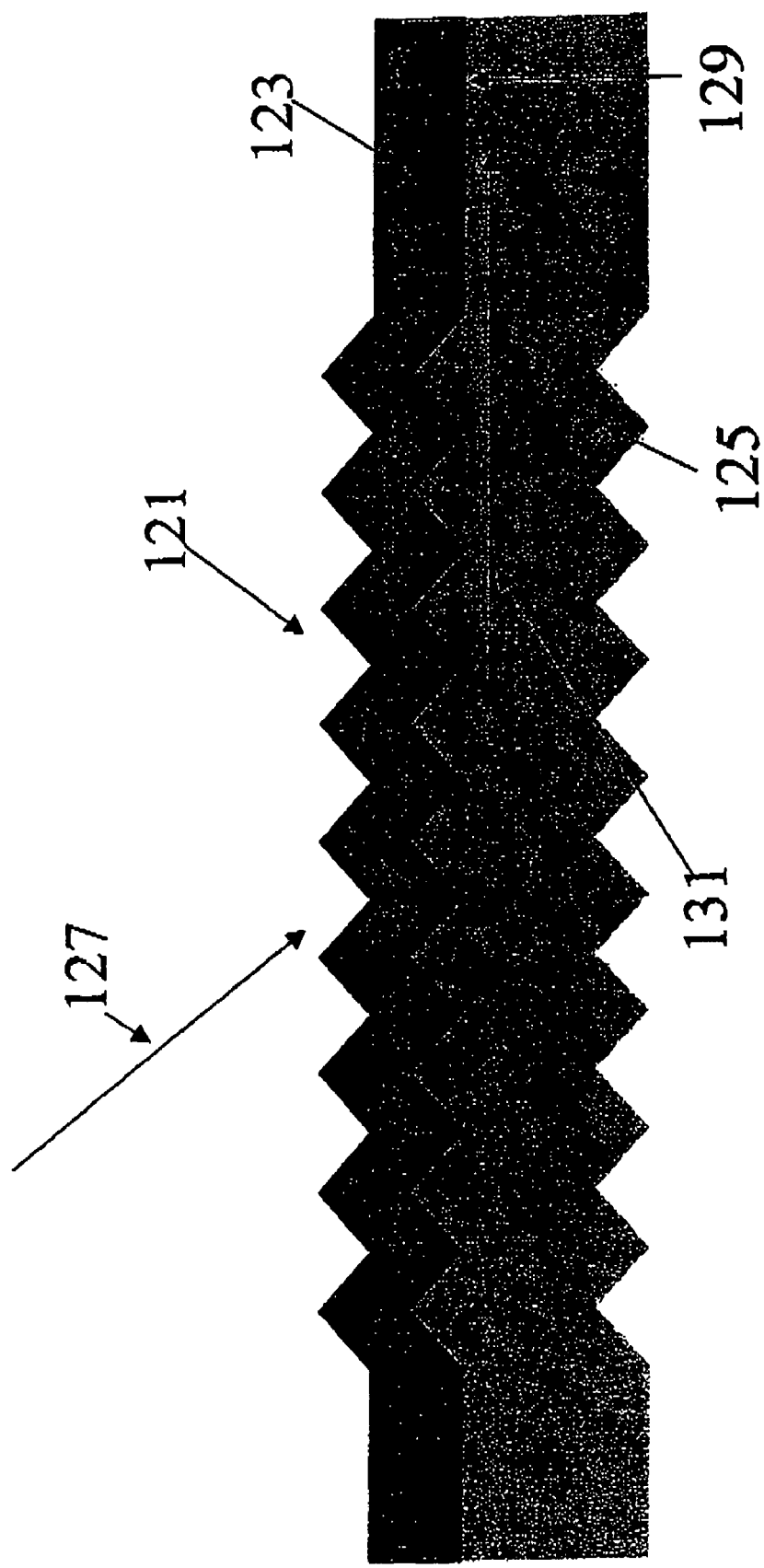
FIG. 9 is a schematic of a cross section of a reaction region of an encoded carrier in accordance with an embodiment of the present invention, the diffraction grating has two corrugated layers.

FIG. 9 is a schematic cross section of an example of the reaction region of the carrier of FIG. 8. The reaction region 121 comprises two corrugated layers 123 and 125. In this particular example, the upper corrugated layer 123 is a dielectric layer and the lower corrugated layer 125 is a metal layer.

Radiation 127 impinges on the upper corrugated layer 123 and travels through this layer 123 to the interface 129 between the upper 123 and lower 125 corrugated layers. Here if the radiation is at the "resonance angle", surface plasmons will be excited and will travel along the plane of the interface as shown by arrow 131.

Upper corrugated later 123 is thin enough such that chemicals attached to the upper surface of the upper corrugated layer 123 affect the resonance conditions for surface plasmon resonance.

Although the dielectric layer 123 is shown as the upper layer, either the dielectric or the metal layer can be used as the uppermost layer in the structure. Typically, the layer which will adhere to the "first type of molecule" will be chosen at the uppermost layer.

Figure 10:
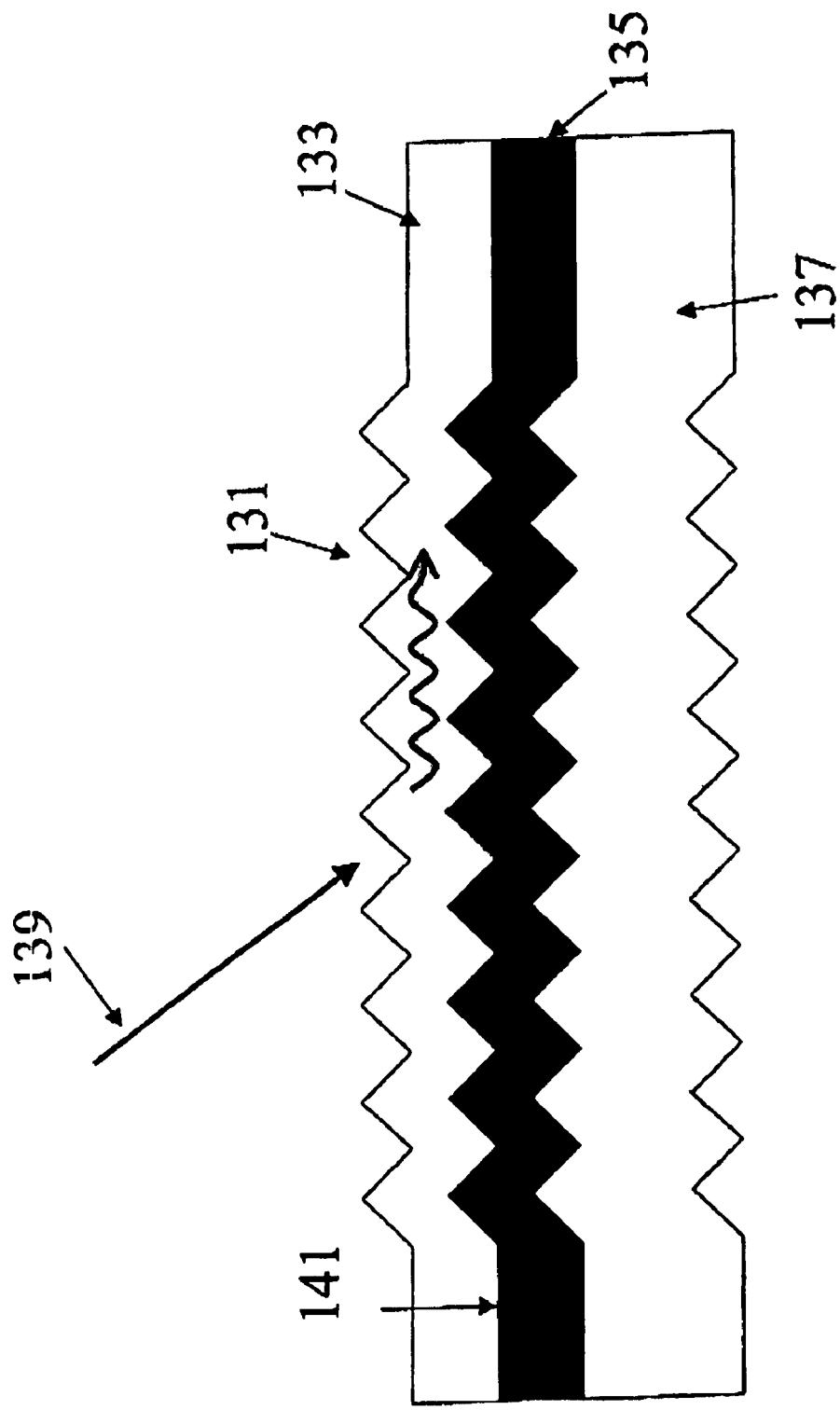
FIG. 10 is a schematic of a cross section of a reaction area of an encoded carrier in accordance with an embodiment of the present invention, the diffraction grating has three corrugated layers.

FIG. 10 schematically illustrates a cross section of a further example of the reaction region of FIG. 8. The reaction region 131, comprises three corrugated layers, an upper metal corrugated layer 133, a middle dielectric corrugated layer 135 and a lower metal corrugated layer 137.

Incoming radiation 139 impinges on the upper corrugated layer 133 and is transmitted through to the interface 141 between the upper corrugated layer 133 and the middle corrugated later 135. If the incident radiation satisfies the resonance condition, it couples to surface plasmon 143 which travels in the metal layer along the plane of the interface.

The upper corrugated layer 133 is thin enough such that chemicals adhering to the upper surface of this layer 133 will affect the surface plasmon resonance condition. The lower corrugated layer 137 is too thick for chemicals adhering to its surface to affect the surface plasmon resonance condition. Thus, the reaction region 131 is "one-sided".

Figure 11:
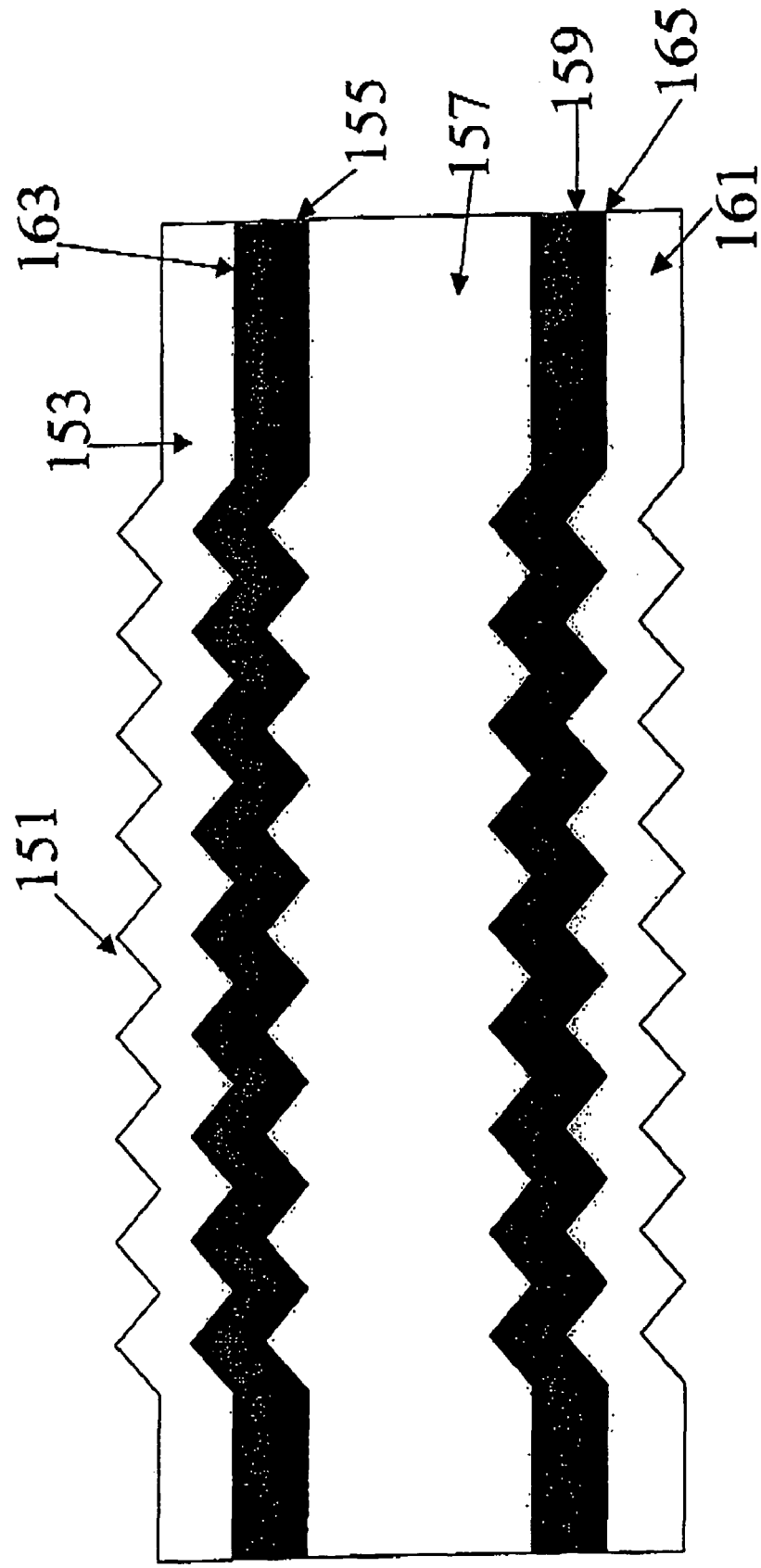
FIG. 11 is a schematic of a cross section of a reaction region of an encoded carrier in accordance with an embodiment of the present invention, the diffraction grating has five corrugated layers.

FIG. 11, is a schematic cross section of a further example of a reaction region for the encoded carrier of FIG. 8. The reaction region 151 is "double sided". Here, upper corrugated dielectric layer 153 is provided overlying and in contact with upper metal layer 155. A thick middle dielectric layer 157 is then provided underneath metal layer 159.

A lower metal layer 159 is then provided on the opposing side of middle dielectric layer 157 to upper metal layer 155. The structure is then finished with lower dielectric layer 161. All layers are corrugated layers.

The middle thick dielectric layer is thick enough to ensure that plasmons generated at the upper interface 163 between the upper dielectric layer 153 and the upper metal layer 155 do not interfere with plasmons generated at the lower interface 165 between the lower metal layer 159 and the lower dielectric layer 161.

The reaction region works in a similar manner to that described with reference to FIG. 10. However, the reaction region can cope with light impinging on either side and thus the reaction region may be analysed regardless of which plane of the encoded carrier is uppermost during the analysis process.

Figure 12:
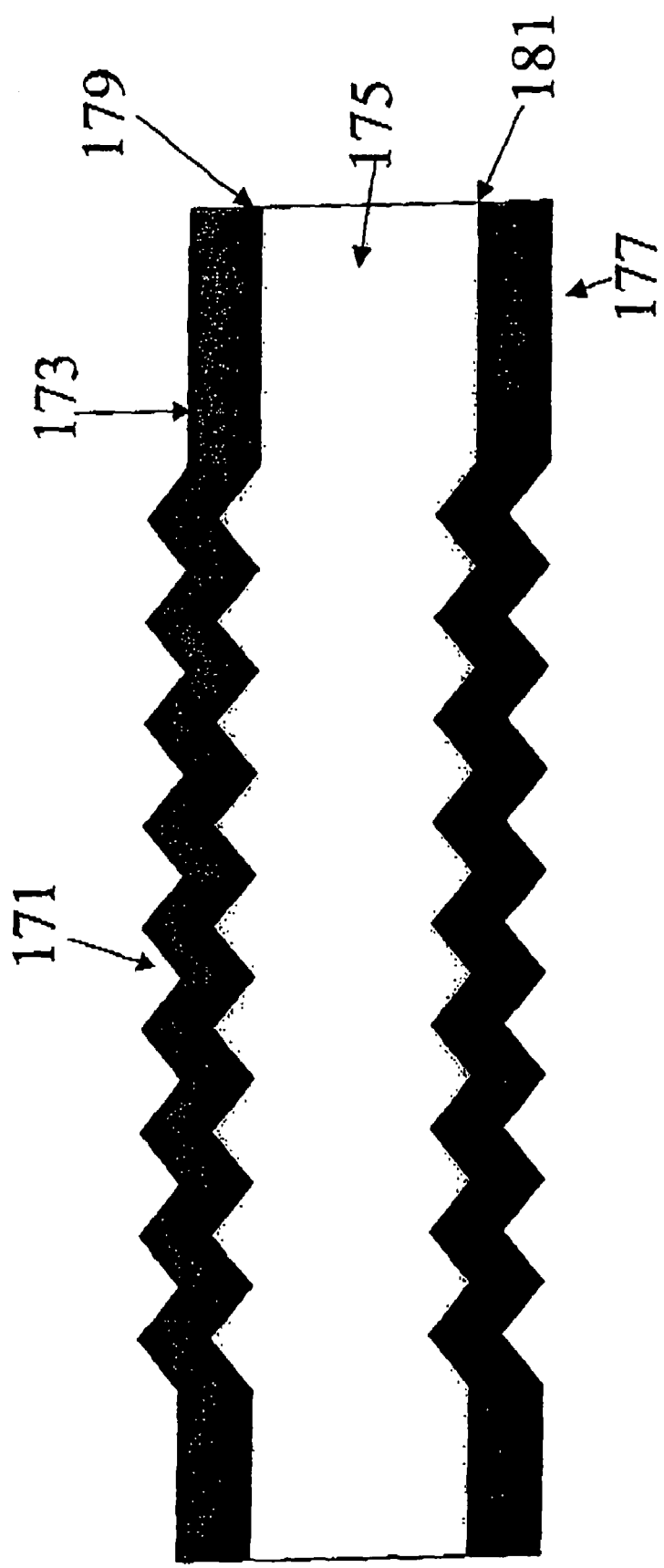
FIG. 12 is a schematic of a cross section of a reaction region of an encoded carrier in accordance with an embodiment of the present invention, the diffraction grating has three corrugated layers.

FIG. 12, is a schematic cross section of a further example of a reaction region for the encoded carrier of FIG. 8. The reaction region 171 is "double sided". Here, upper corrugated metal layer 173 is provided overlying and in contact with middle dielectric layer 175. Lower metal layer 177 is provided on the opposite side of said middle dielectric layer 175 to said upper metal layer 173.

The reaction region works in a similar manner to that described with reference to FIG. 10. However, the reaction region 171 can cope with light impinging on either side and thus the reaction region may be analysed regardless of which plane of the encoded carrier is uppermost during the analysis process.

The middle thick dielectric layer 175 is thick enough to ensure that plasmons generated at the upper interface 179 between the upper metal layer 173 and the middle dielectric layer 175 do not interfere with plasmons generated at the lower interface 181 between the lower metal layer 177 and the middle dielectric layer 175.

Figure 13:
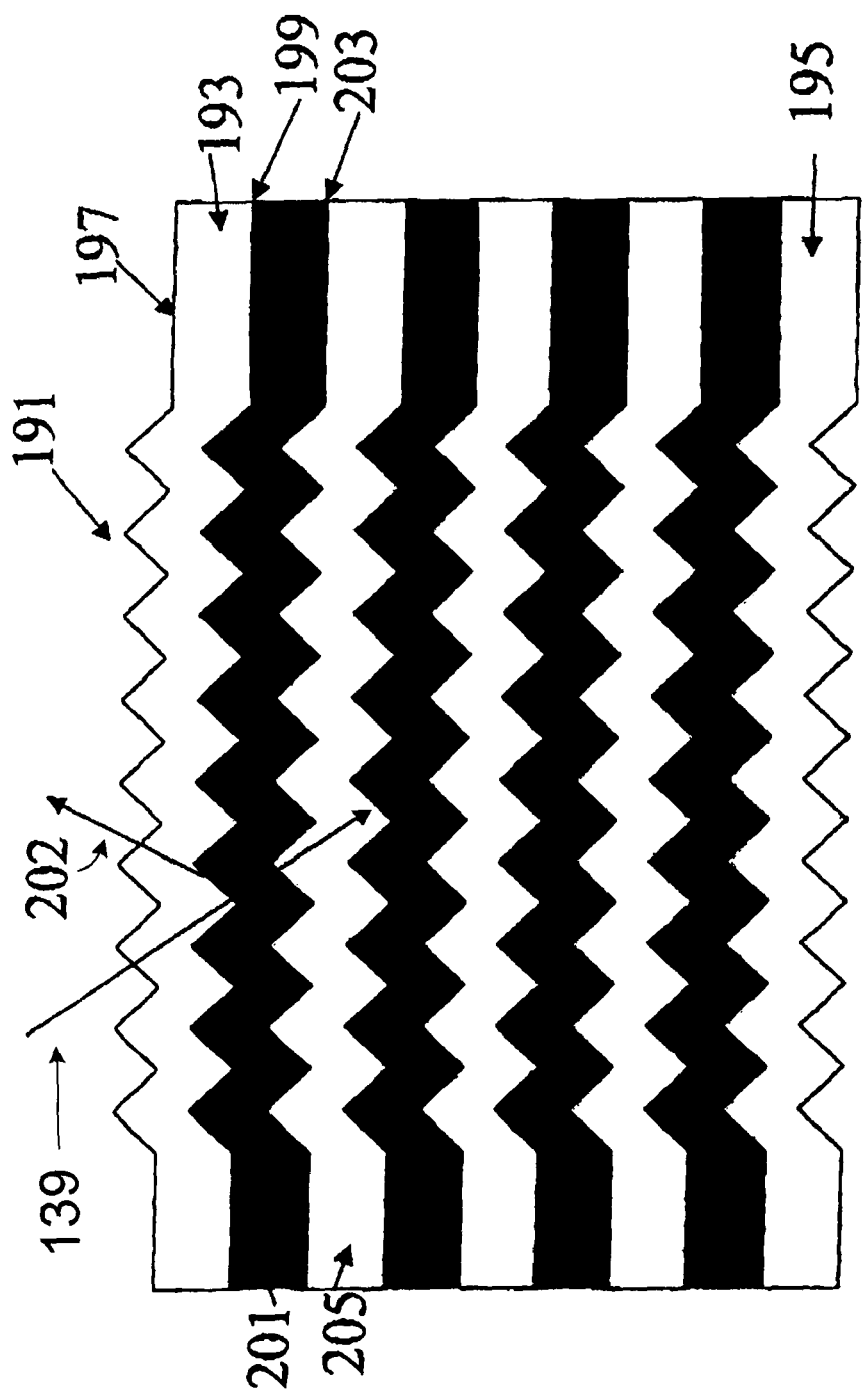
FIG. 13 is a schematic cross section of a reaction region of an encoded carrier in accordance with an embodiment of the present invention, the diffraction grating has multiple periodic corrugated layers.

FIG. 13, is a schematic cross section of a further example of a reaction region for the encoded carrier of FIG. 8. The reaction region 191 is again "double sided". The reaction region comprises alternating metal and dielectric corrugated layers, the structure being terminated with an upper dielectric layer 193 and a lower dielectric layer 195. The structure is periodic.

The particular structure of FIG. 13 has 9 layers and hence 8 interfaces at which surface plasmons may be generated. When light impinges on the upper dielectric surface 197 it travels through the first dielectric layer 193 to the first interface 199 between the first dielectric layer 193 and the first metal layer 201. This light will be reflected along path 202. The amount of radiation reflected will depend on whether or the conditions for surface plasmon resonance are satisfied.

Some of the incident radiation will pass through the first metal layer 201 to second interface 203 between first metal layer 201 and second dielectric layer 205 and hence the radiation may also couple to a surface plasmon mode at the second interface 203.

Radiation may penetrate further into the structure and excite surface plasmons at a plurality of interfaces thus outputting radiation which has reflected from a number of different interfaces within the structure. As the structure is symmetric, it is double sided.

Figure 14:
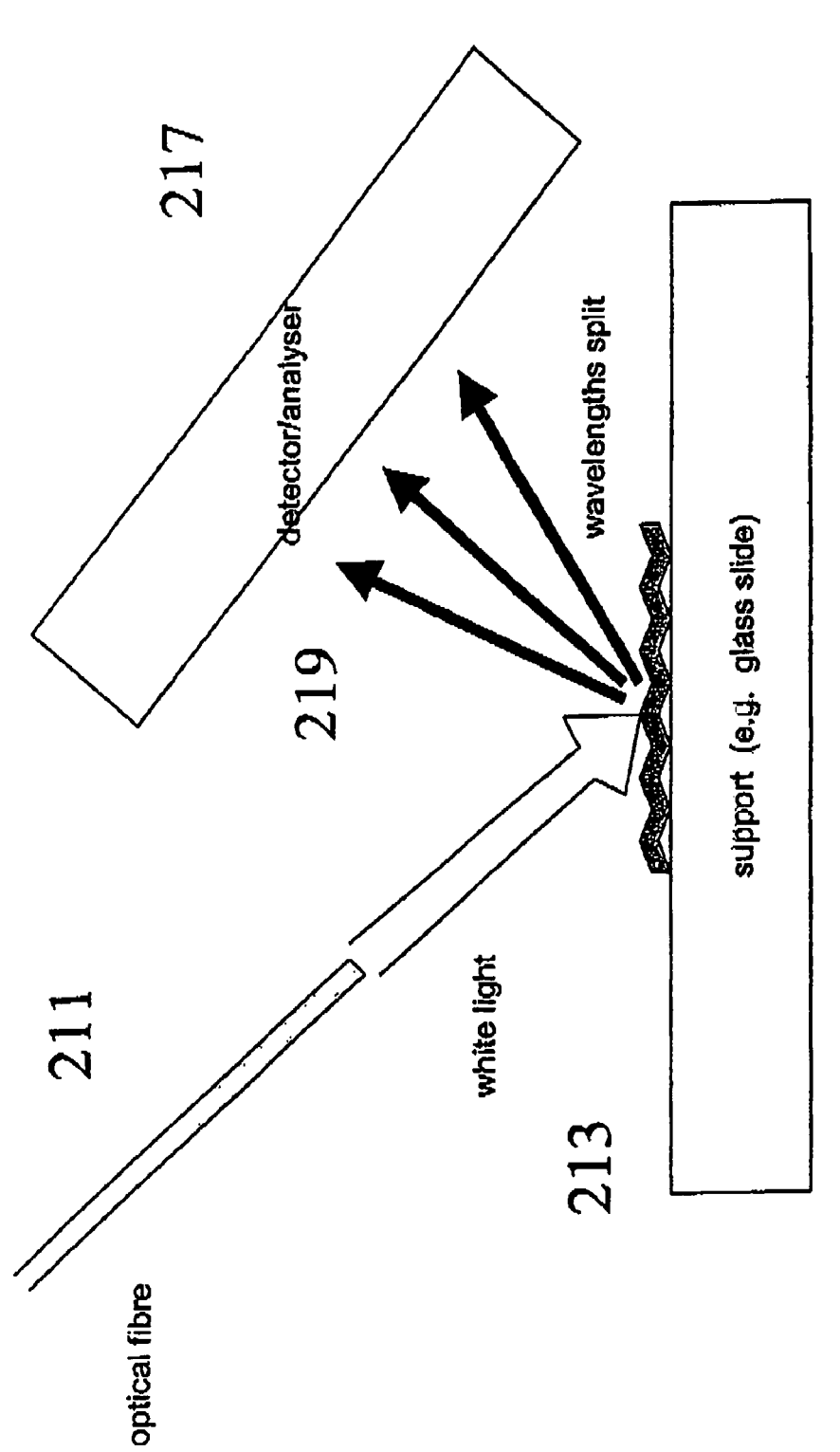
FIG. 14 illustrates schematically a measurement method in accordance with an embodiment of the present invention.

An example of an apparatus which may be used to measure changes in the surface plasmon resonance condition has been described with reference to FIG. 3. In the apparatus of FIG. 3, the laser 25 and the detector 31 are moved to establish the resonance angle. FIG. 14 schematically illustrates a further type of apparatus which may be used to measure changes in the surface plasmon resonance condition.

The apparatus comprises a polychromatic source, which in this particular example is an optical fibre 211 delivering white light. The white light is directed onto the encoded carrier 213 which is located on a substrate 215. The substrate 215 may be glass.

The white light is scattered by the diffraction grating on encoded carrier 213 and is separated into its colour components 219. These are then detected by detector 217.

When molecules of a first type are attached to encoded carrier 213, the angle of the incident radiation is such that the resonance condition will be satisfied for one of the colour components 219 of the radiation. The detector 217 will thus determine that one of the colour components has a substantially reduced amplitude.

When the target molecules attach to the molecules of the fist type, the angle of the incident radiation will then satisfy the surface plasmon resonance condition for a different colour component, thus it is possible to determine if the reaction has taken place by determining which colour component had a reduced amplitude before and after the reaction.

By measuring the size of the reduction of the amplitude it is possible to determine information about the reaction kinetics.

Previously, the presence of the target molecule has been detected by measuring the amplitude of the reflected radiation, for example, see FIGS. 3 and 14. However, is it also possible to detect the presence of the target molecule by measuring changes in the polarisation of the reflected radiation which are affected by the presence of the target molecule.

Figure 15:
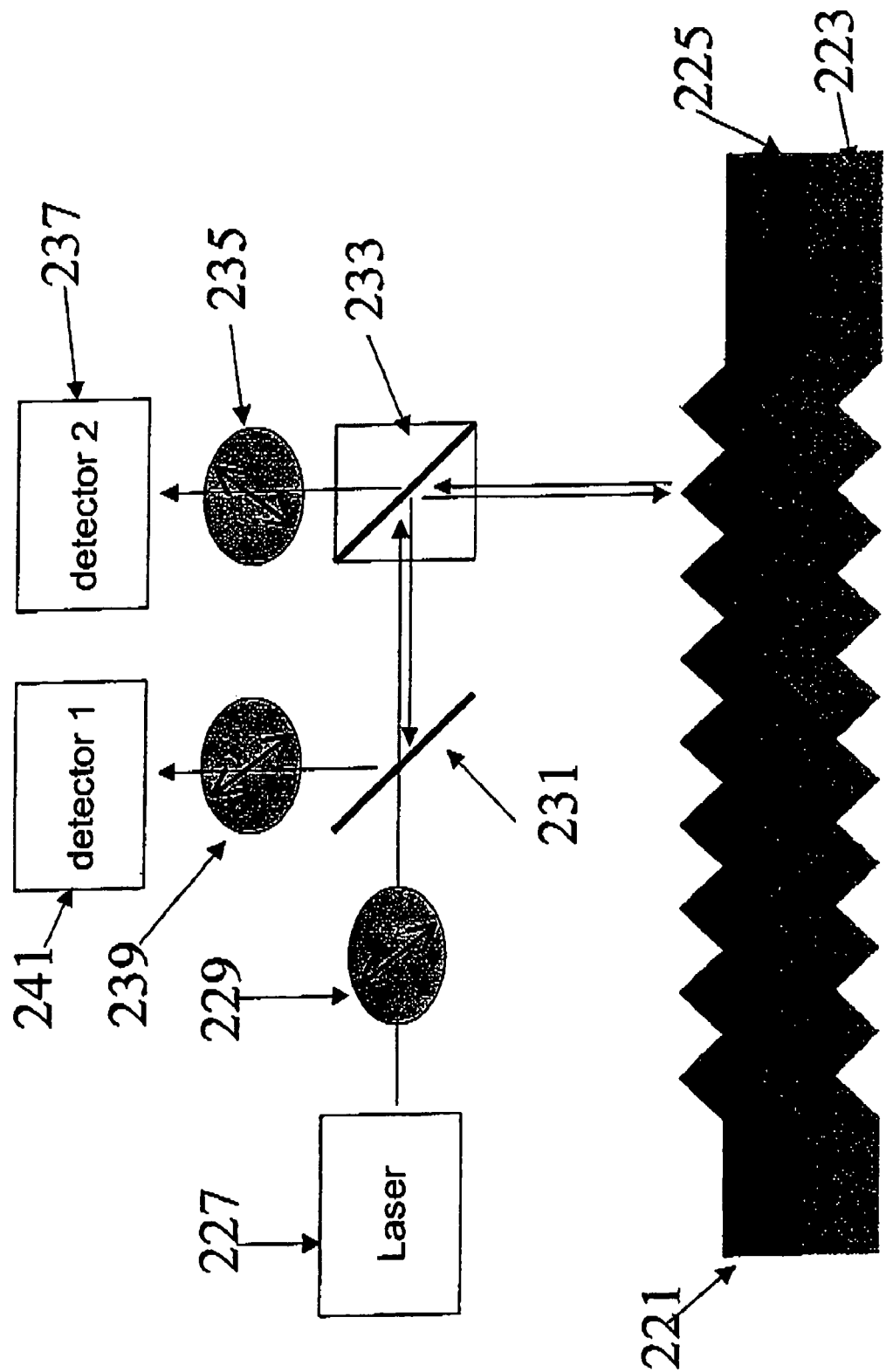
FIG. 15 illustrates schematically a further measurement method in accordance with an embodiment of the present invention.

FIG. 15 illustrates an apparatus which may be used to detect changes in the polarisation of reflected radiation. A zero order or non-diffractive diffraction grating, is a diffraction grating whose Bragg vector is sufficiently large such that all diffracted orders (except the zero) are evanescent. In such a diffraction grating which is typically a small pitch grating, the grating may cause the polarisation of reflected radiation to be rotated by up to 90°. Whether or not polarisation of incident radiation is rotated may be affected by the presence or absence of target molecules attached to the probe molecules on the surface of the diffraction grating.

FIG. 15 schematically illustrates apparatus for performing a polarisation measurement on encoded carrier 221. The encoded carrier may be any of the types previously described. In this particular example, the encoded carrier 221 comprises an upper corrugated dielectric layer 223 and a lower corrugated metal layer 225 to form a two-layer diffraction grating. The diffraction grating may also be a planar grating as described with reference to FIGS. 4 and 5. The grating may also comprise just a single layer.

Laser 227 generates radiation of a particular wavelength. The radiation is first passed through polarising filter 229 which polarises the radiation in a first polarisation direction. The radiation is passed through selected transmission ratio mirror 231. The beam then impinges on polarising beam splitter 233, the polarisation of the incident radiation and the setting of polarising beam splitter 233 is such that the radiation is reflected by the polarising beam splitter 233 onto encoded carrier 221. The radiation incident on encoded carrier 221 is normal to the plane of encoded carrier 221. The polarisation of the incident radiation is also arranged so that it is at an angle of 45° to the corrugations when it reaches the encoded carrier 221.

Radiation is then reflected from encoded carrier 221. If the polarisation is not rotated by the diffraction grating, the light will be reflected from the encoded carrier 221 and will be reflected again by polarising beam splitter 233 towards selected transmission ratio mirror 231 and then reflected through polarising filter 239 into first detector 241. Polarising filter 239 has the first polarisation direction of polarisation filter 229.

If the diffraction grating rotates the polarisation of the radiation by 90°, the reflected radiation will be transmitted through the polarising beam splitter 233 through polarising filter 235 and into second detector 237. Polarising filter 235 has a polarising direction which is orthogonal to the first polarisation direction of filter 229.

The encoded carrier 221 may be configured by altering the pitch of the grating and the material of the grating such that when only probe molecules are present on the surface of the grating, radiation is reflected with one polarisation direction and when target molecules have bound to the probe molecules, radiation is reflected with a different polarisation. The presence of the target molecules does not have to rotate the polarisation by 90°. Any variation in the polarisation angle can be detected by the above described apparatus since the amplitude of radiation detected at the first and second detectors will vary dependent on the angle of polarisation of the reflected light.

Figure 16:
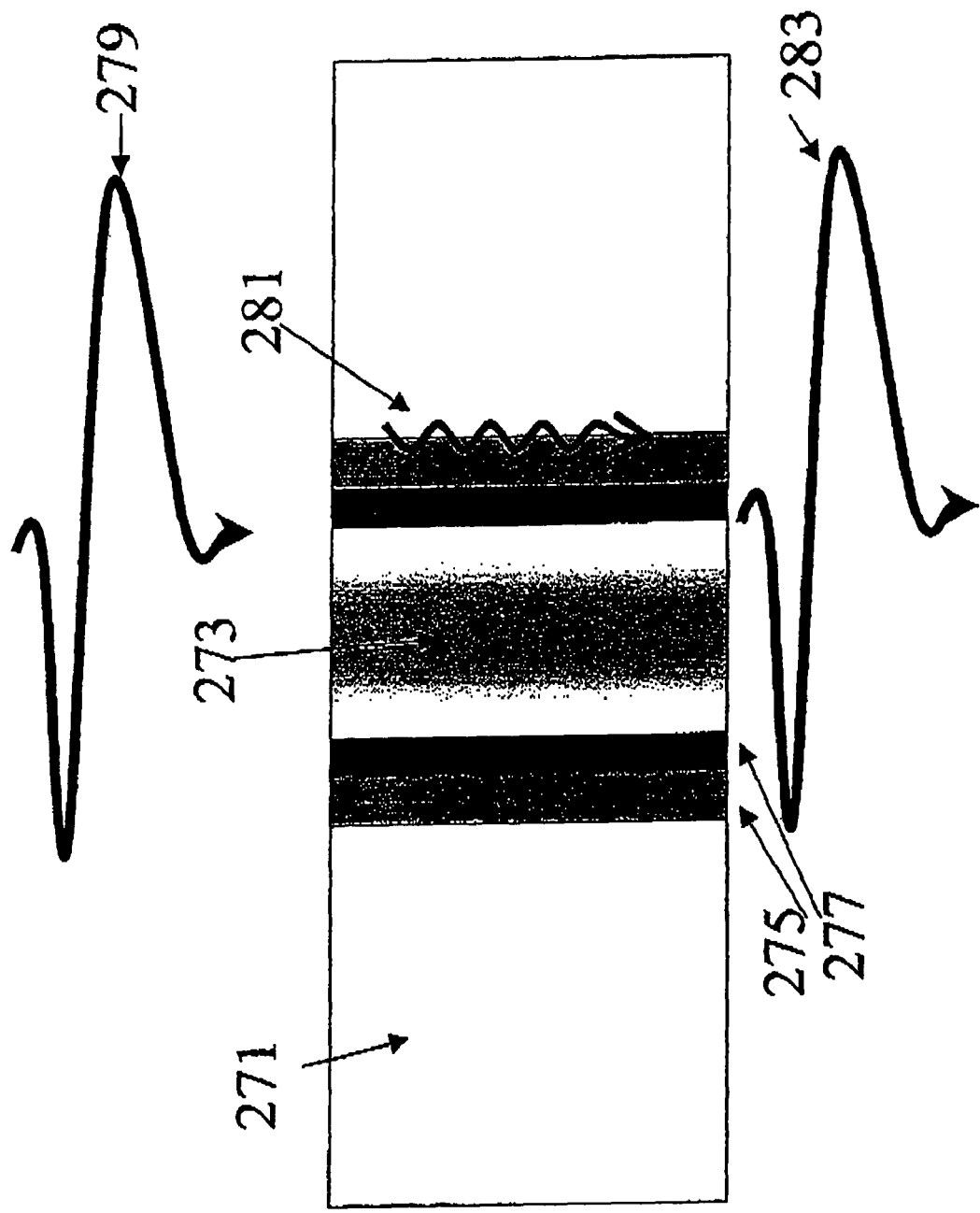
FIG. 16 schematically illustrates a cross section of a carrier in accordance with an embodiment of the present invention.

Although the above description has concentrated on detecting the presence of target molecules by analysing reflected radiation, the target molecules may also effect the transmission properties of any coded carrier. FIG. 16 schematically illustrates an encoded carrier 271 with a hole 273 which extends throughout the whole of the encoded carrier 271. The encoded carrier 271 comprises a metal film, in this particular example, a silver film is used.

In the example of FIG. 16, the walls of hole 273 have been lined with probe molecules 275. These probe molecules have reacted with target molecules 277 which then coat the inside of the hole 273. When photons 279 are incident in the region of the hole, some of the radiation passes directly through the hole 273 while some of the radiation excites surface plasmons 281 at the interface between the part of the encoded carrier 271 forming the walls of the hole and probe molecules 275. These surface plasmons 281 propagate through the structure and serve to emit radiation 283 at the other side of the encoded carrier 271. Since radiation passes both through the centre of the hole 273 unimpeded and along the sides of the holes due to the excitation of surface plasmons 281, more radiation appears to be transmitted through the encoded carrier 271 than expected if radiation just simply passed through the holes. How much radiation is also transmitted due to surface plasmons 281 depends on the molecular lining 275 and 277 of hole 273. Therefore, the presence or absence of the target molecule layer 277 affects the amplitude of radiation transmitted through encoded carrier 271.

Figure 17:
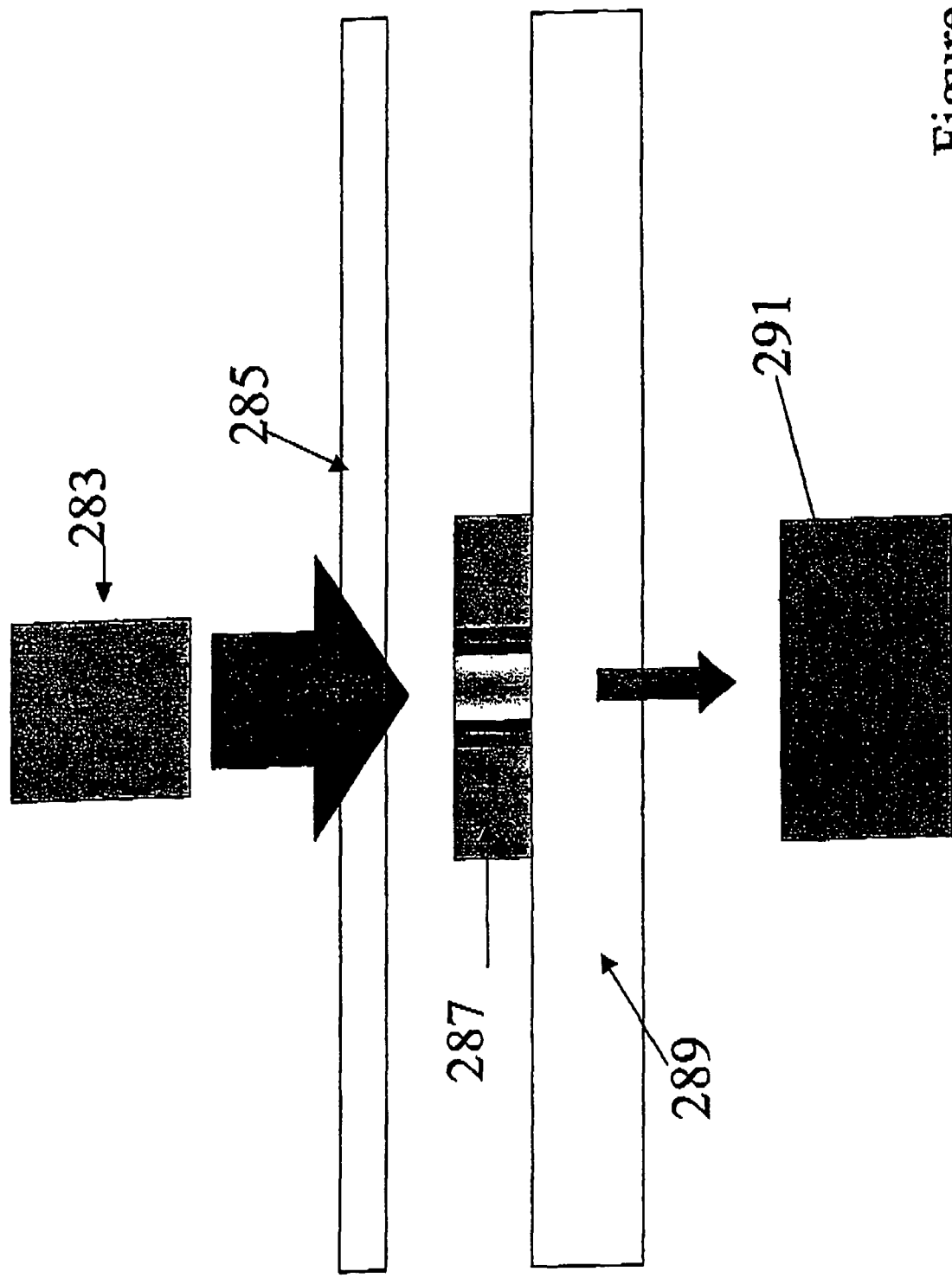
FIG. 17 is a schematic of a measuring apparatus for the carrier of FIG. 16.

FIG. 17 schematically illustrates a measurement apparatus for measuring this effect. Radiation is generated by laser 283 which transmits radiation through window 285 to encoded carrier 287. The encoded carrier is the same as that described with reference to FIG. 16 and will not be described further here. The encoded carrier sits on a transparent support such as glass slides 289. Radiation from laser 283 which has been transmitted through window 285, through encoded carrier 287 and through glass support 289 is then detected by detector 291. The encoded carrier 287 is provided in either a gas or a liquid medium between window 285 and glass support 289.

The above arrangement may be used to detect whether or not the target molecules have bonded to the probe molecules since the amplitude of radiation transmitted through encoded carrier 287 will vary dependent on whether or not the target molecules have reacted with the probes.

Figure 18:
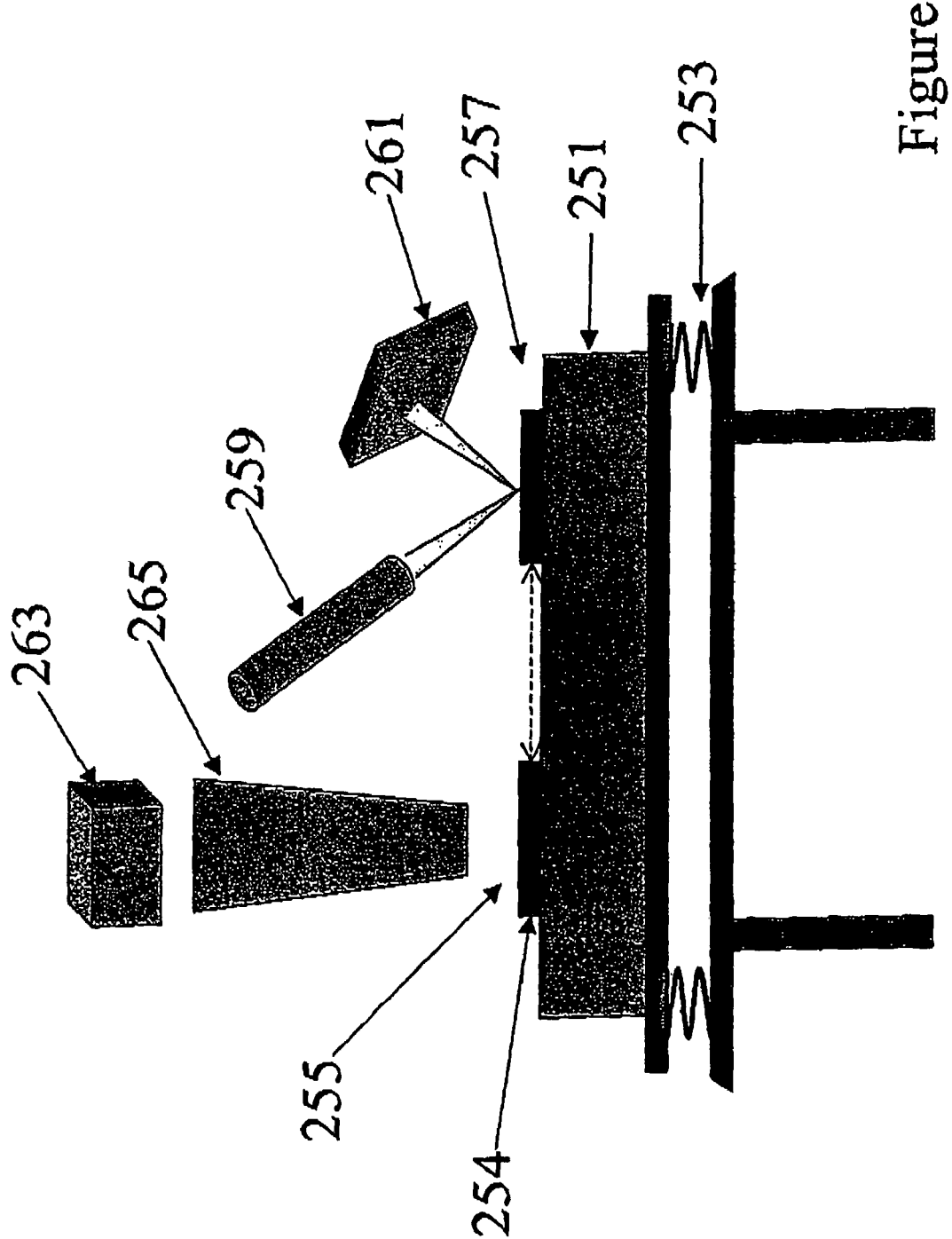
FIG. 18 is a schematic of a reading apparatus for the encoded carriers of the present invention.

FIG. 18 schematically illustrates a reading apparatus in accordance with an embodiment of the present invention. The reading apparatus comprises a stage 251 which is provided on anti-vibration table 253. The stage is capable of moving a sample placed on the stage in either the x or y directions and also rotating the samples.

The stage 251 is configured to move an encoded carrier 254 placed on the stage between a reading area 255 and an analysis area 257.

In the reading area 255, the code is read. The reading apparatus comprises digital camera 263 and optical zoom lens 265. Analysis software is also provided to be able to read the bar code and possibly, an optical character recognition package will be provided if the code is an alpha-numeric code. These techniques are well established and will not be discussed further here. The code can be read from any orientation. However, it is important to be able to determine the orientation of the carrier in the reading area so that the diffraction grating is correctly oriented for analysis in the analysis area 257.

The analysis area 257 is configured to perform surface plasmon resonance measurements in order to determine whether or not the target molecule has reacted with molecules on the encoded carrier. The analysis apparatus which analyse the carrier in the analysis area comprise a radiation source 259 and a detector 261. The apparatus are also shown schematically and examples of the apparatus have been described with reference to FIGS. 3, 14, 15 and 17.

FIGS. 19A and 19B are cross sectional views, showing two stages in the production of an encoded carrier according to an embodiment of the invention. In the embodiments described with reference to the previous figures, the encoded carrier has a dielectric layer and a metal layer, for simplicity, only a single layer is shown in FIGS. 19A and 19B.

FIG. 19A, a soluble substrate 301 has a raised pattern 303 provided on lower substrate level 305. The pattern 303 defines an upper level 307 which is separated from the lower level 305 by substantially vertical side walls 309.

The soluble substrate may be positioned by wet or dry etching techniques such as RIE. Alternatively, the substrate may be made from a mould.

FIG. 19A is a cross section through pattern 303, such that the pattern 303 appears as a plurality of vertical pillars. In reality the pillars are elongated into the plane of the paper and are connected at their ends to form, in this embodiment, a continuous structure as indicated by the dotted lines.

In FIG. 19A, a dielectric and a metal layer are deposited onto the substrate 301 such that there is an upper coating 313 formed on upper level 307 and a lower coating 317 formed on lower level 305. The deposition is directional such that neither of the layers are provided on the side walls 309. The side walls 309 cause the coating 313 to be discontinuous from the lower coating 317. Due to the overall shape of pattern 303, the sections of upper coating 313 are all connected to each other to form an essentially planar structure.

The substrate 301 is dissolved in order to release the upper coating 313 as shown in FIG. 19B. This upper coating forms the encoded carrier. By appropriate patterning of the substrate 301, both the code area and the reaction region may be patterned using this technique.

FIG. 19B shows the stage of the process after the substrate 301 has been partially dissolved to release the carrier 313. The substrate is dissolved by placing it in a flowing solvent. The flow direction of the solvent is indicated by the arrow.

FIGS. 20A and 20B show two stages in a method of making a carrier with a corrugated diffraction grating. A substrate 321, as shown in perspective view in FIG. 20A, is provided with a three dimensional relief pattern 323 on its surface. The pattern 323 comprises "V" shaped indents 325 and indents with vertical side walls 327.

FIG. 20B shows an example of material to form an encoded carrier deposited onto the substrate of FIG. 20A. The material is deposited over the relief of the substrate 321. Material deposited over the V-shaped indents 325 takes on a corrugated form so that it may function as a diffraction grating. Material deposited over the indents with vertical side walls 327 may form part of the code region or may be used to separate adjacent encoded carriers.

Figure 19:
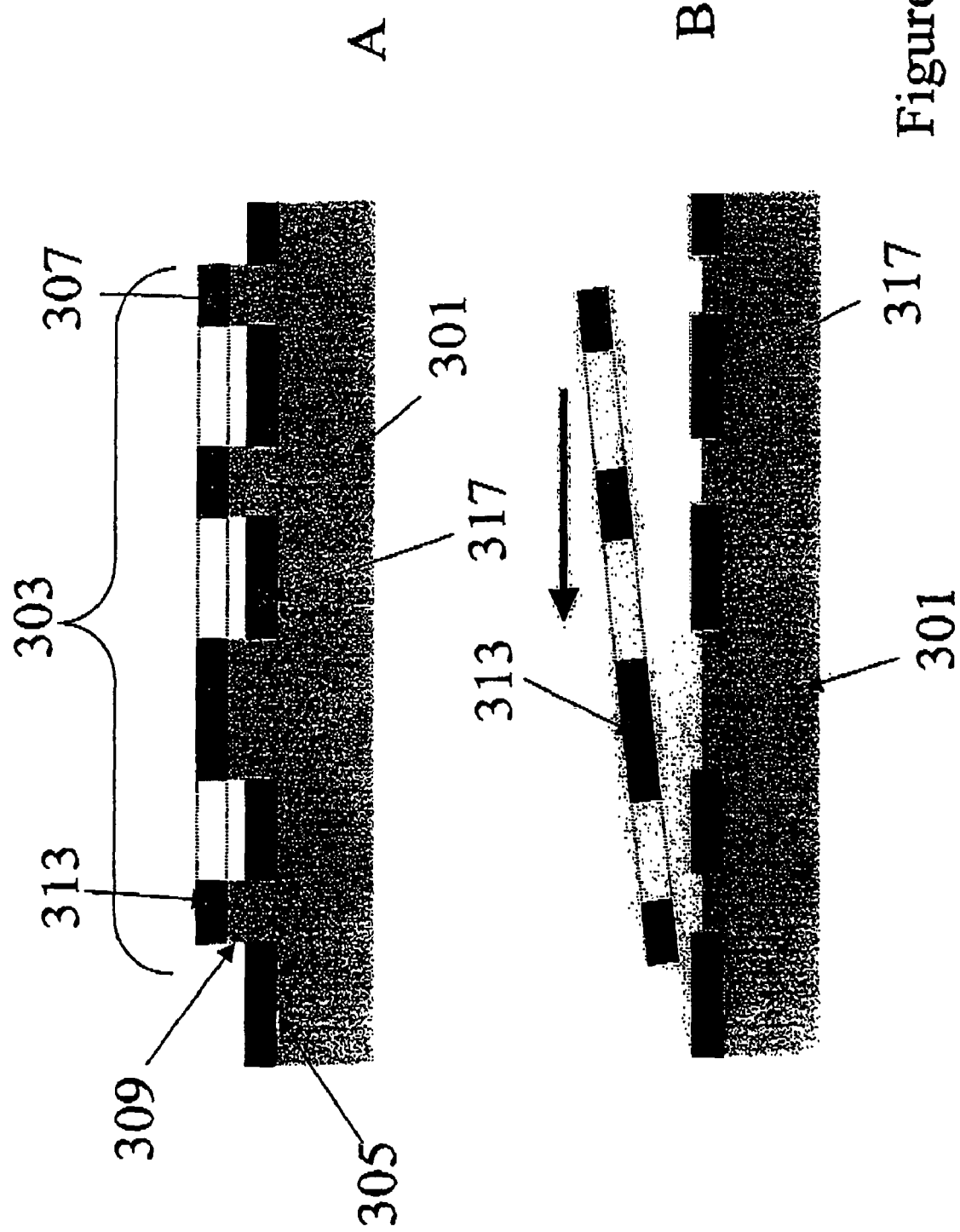
FIGS. 19a and 19b are schematics showing a manufacturing method for a carrier in accordance with an embodiment of the present invention.
Figure 20:
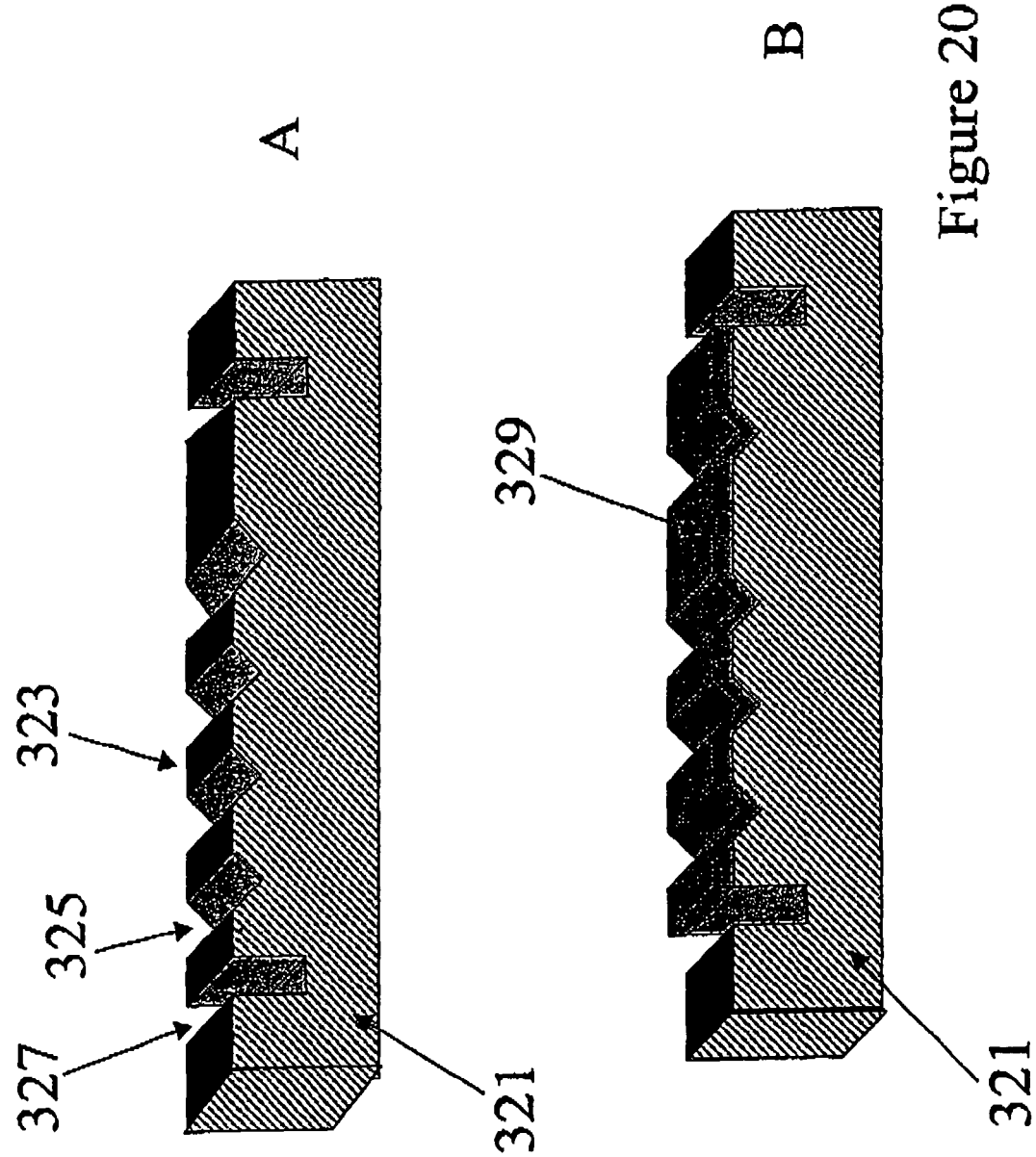
FIGS. 20a and 20b are schematics showing a manufacturing method for a carrier in accordance with a further embodiment of the present invention.

The indents with the steep side walls in both FIGS. 19 and 20 may be used to form holes which are bounded on each side or may be used to form holes which are open to the edge of the carrier. To avoid debris getting caught in the holes, it is preferable if the code is formed from bars or characters which are open to the edge of the carrier.

Figure 21:
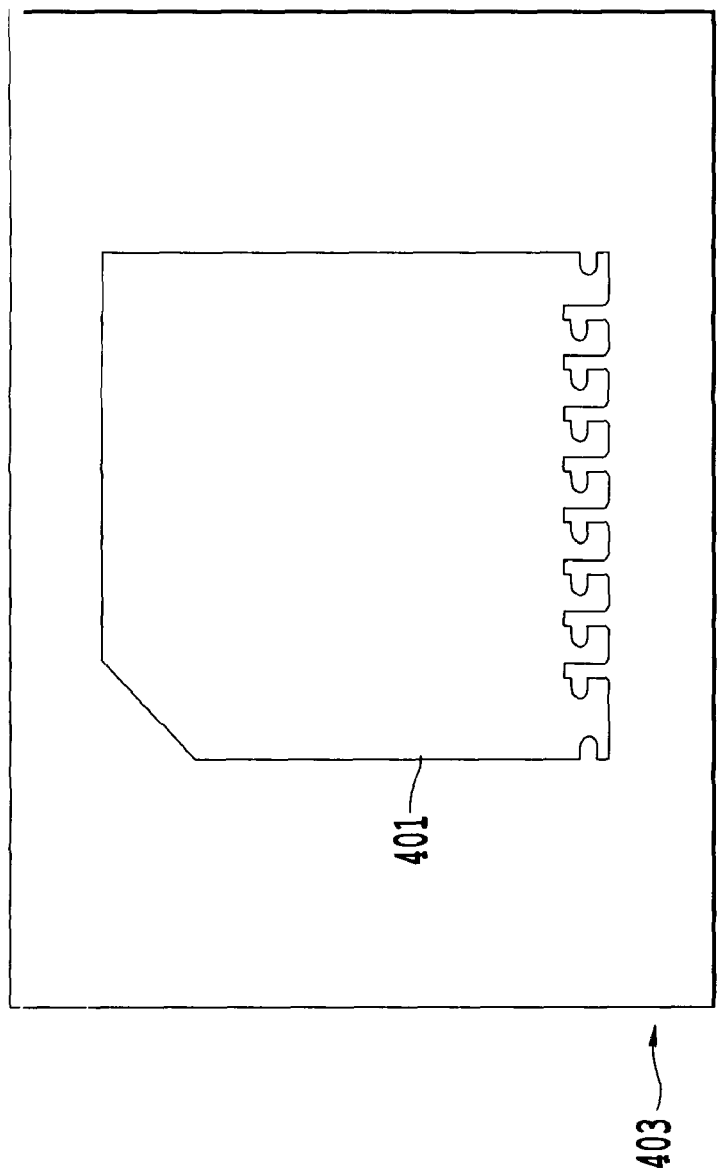
FIG. 21 is an image of a carrier useful for understanding the present invention.

FIG. 21 is an image of a carrier 401 taken using an electron microscope. The carrier has an alphanumeric code 403 which is open to the edge of the carrier. The carrier is 100 µm by 110

μm. In this example useful for understanding the invention, no diffraction grating is present on the reaction region.

Figure 22:
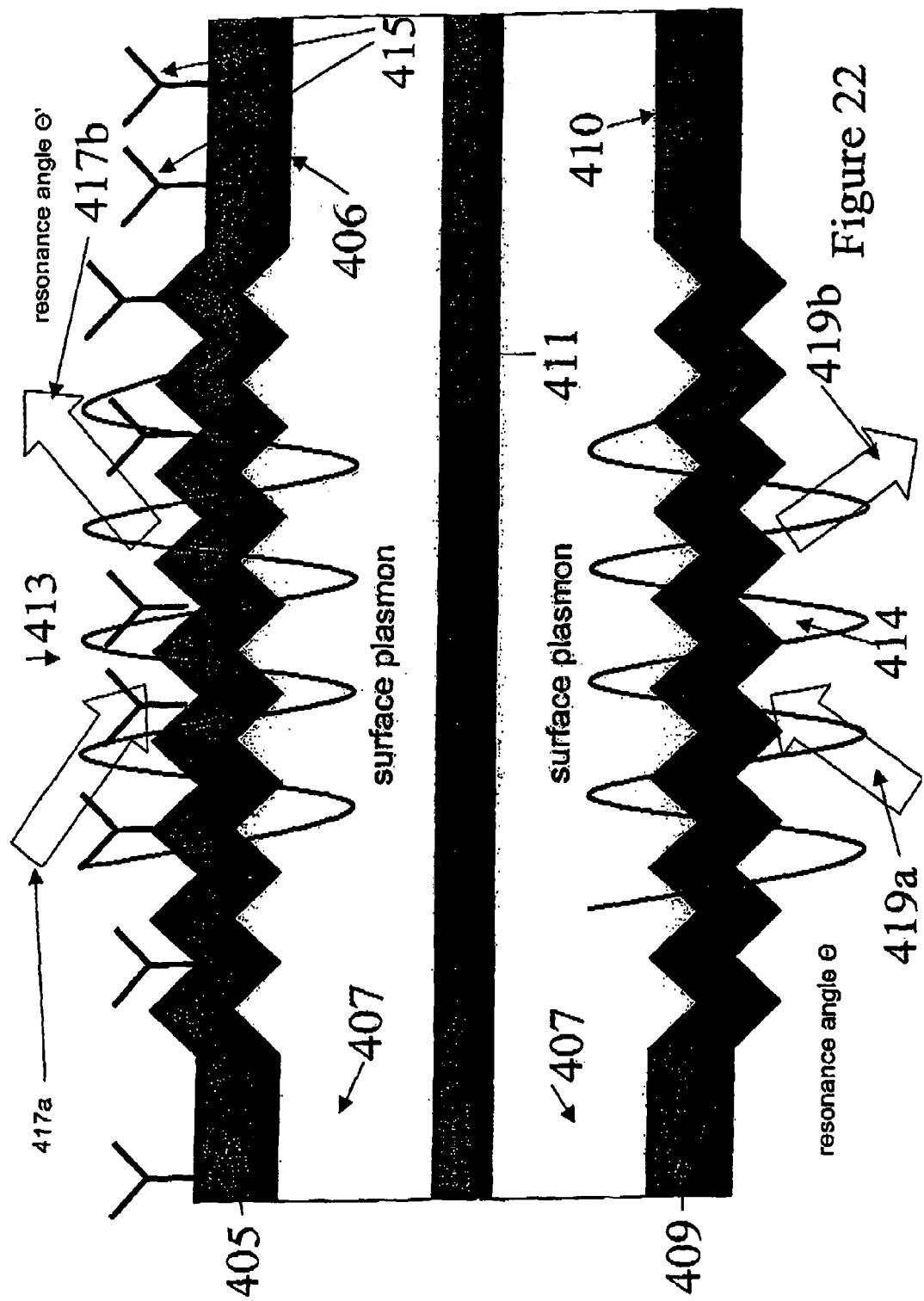
FIG. 22 is a schematic of a cross section of a reaction region of an encoded carrier in accordance with an embodiment of the present invention, the diffraction grating has three corrugated layers.

FIG. 22 shows a schematic cross section of a further example of a reaction region for the encoded carrier of FIG. 8. The carrier in this figure is similar to the carrier depicted in FIG. 12, however although the carrier comprises reaction regions on both sides, only one of the two sides is functionalised such that it will be affected by the presence of a target molecule.

In FIG. 22 upper corrugated metal layer 405 is provided overlying and in contact with middle dielectric layer 407. Lower metal layer 409 is provided on the opposite side of said middle dielectric layer 407 to said upper metal layer 405. A barrier 411 can optionally be included in the dielectric layer 407 to prevent cross-talk between the upper and lower metal layers.

A reaction region 413 is provided on the upper layer 405. The region depicted comprises a plurality of chemical species 415 (similar to those described in relation to FIG. 1). The reaction region 414 of the lower layer 409 does not comprise the chemical species.

A beam of radiation 417a incident on the upper surface 405 will generate plasmons at the interface 406 between the upper metal layer 405 and the dielectric layer 407. A beam of radiation 419a incident on the lower surface 409 will generate plasmons at the interface 410 between the lower metal layer 409 and the dielectric layer 407.

As described with reference to FIG. 1 at the appropriate resonance condition there will be a steep fall in radiation reflected from the surface of the carrier since this radiation is now absorbed by coupling to the surface plasmon mode. Radiation 417b reflecting from the upper surface has a resonance angle of θ'. Radiation 419b reflecting from the lower surface 409 has a resonance angle of θ.

Figure 23:
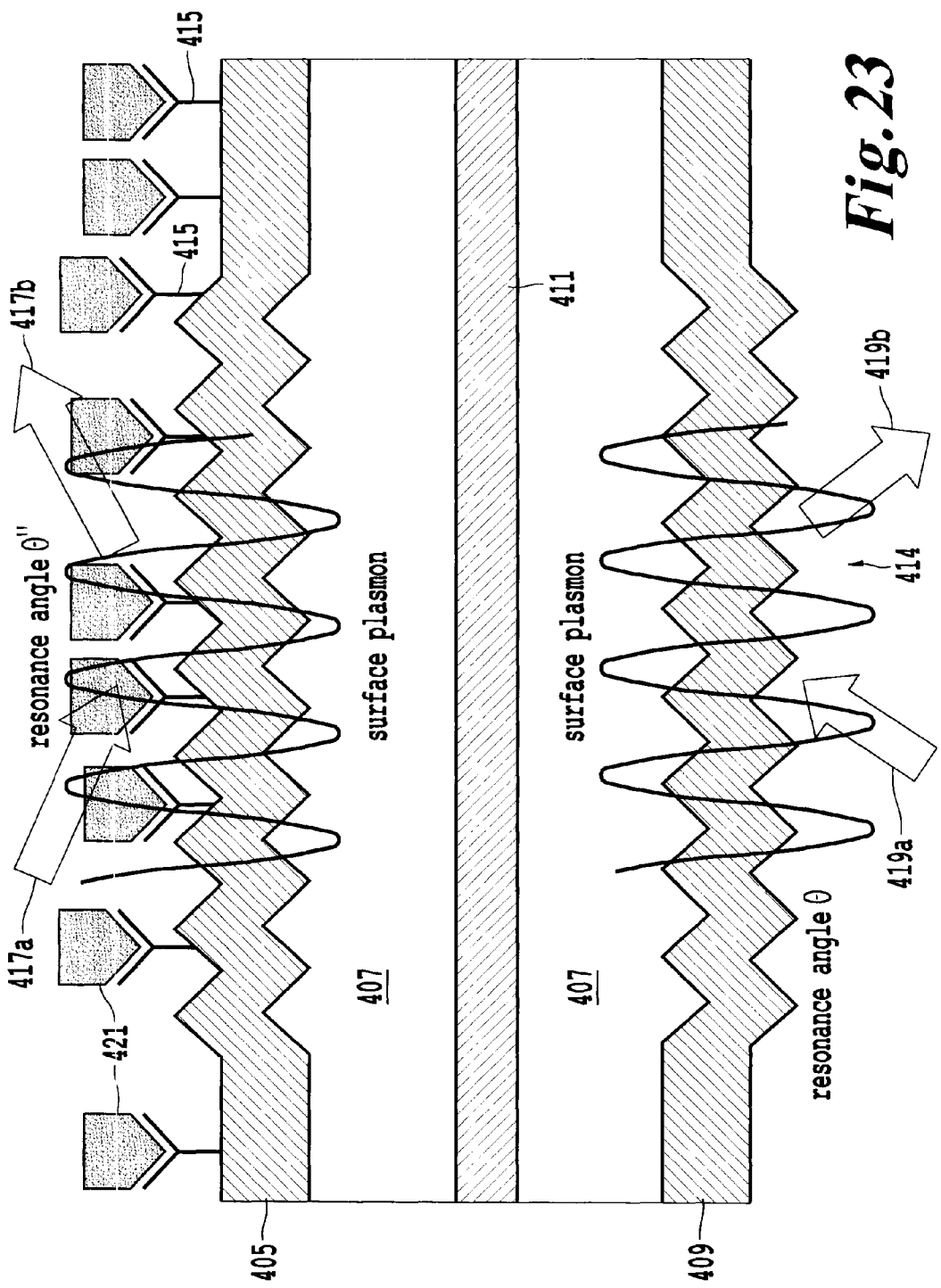
FIG. 23 shows the carrier of FIG. 22 following reaction with a target molecule.

FIG. 23 shows the carrier of FIG. 22 following reaction with molecules 421 (like features are denoted by like numerals). As shown the molecules 421 have attached to the chemical species 415 and the resonant angle with respect to the upper layer 405 has changed from θ' to θ".

The reaction region 414 on the lower surface 409 however has not been altered by the presence of the molecules 421 and therefore its resonance angle is unchanged at θ.

The carrier shown in FIGS. 22 and 23 therefore comprises a double sided structure wherein one side is functionalised such that the presence of a certain molecule will affect the surface plasmon characteristics of that side and the second side is not functionalised such that the surface plasmon characteristics of the second side are unaffected by the presence of the target molecules 421. This carrier structure provides a means of preventing false measurements resulting from external factors such as thermal or vibrational conditions. If both sides exhibit resonance angle changes then this is likely due to external factors. However, if only one side exhibits a resonance angle change then this is likely to be due to the presence of target molecules.

Where the two sides exhibit a dissimilar change in resonance angle, the net change due to the presence of target molecules can be obtained from the difference between the two observed changes.

The invention claimed is:

1. An encoded carrier comprising:
a code region having a code; and
a reaction region separate from said code region, said reaction region having a variation in its refractive index or dielectric constant in a direction generally parallel to the surface of the reaction region, wherein the reaction region comprising a metal/dielectric interface is configured to support surface plasmons and said variation in the refractive index is configured to couple incident radiation to surface plasmons excited by said radiation.

2. A carrier according to claim 1, wherein said variation in the refractive index is provided by a diffraction grating.

3. A carrier according to claim 2, wherein said diffraction grating is one dimensional.

4. A carrier according to claim 2, wherein said diffraction grating is two-dimensional.

5. A carrier according to claim 2, wherein said diffraction grating is a planar structure.

6. A carrier according to claim 2, wherein said diffraction grating comprises a corrugated structure.

7. A carrier according to claim 2, wherein said reaction region comprises a dielectric layer and a metal layer.

8. A carrier according to claim 2, wherein the diffraction grating is a zero order grating.

9. A carrier according to claim 1, wherein the variation in the refractive index is provided by a plurality of holes which extend through the whole of said reaction region.

10. A carrier according to claim 9, wherein the reaction region comprises a metal layer.

11. A carrier according to claim 1, wherein said code is an alphanumeric code.

12. A carrier according to claim 1, wherein said code is a barcode.

13. A carrier according to claim 1, wherein said carrier is generally planar and said code is provided at or close to two or more edges of said carrier.

14. A carrier according to claim 1, wherein said carrier is generally planar and said code can be uniquely identified regardless of which plane of the carrier is uppermost.

15. A carrier according to claim 1, wherein the code extends through the whole of the width of said carrier.

16. A carrier according to claim 1, wherein the code is provided at the edges of the carrier and each character of the code extends to an edge of the carrier.

17. A carrier according to claim 1, wherein the encoded carrier is less than 400 μm by 400 μm.

18. A carrier according to claim 1, wherein molecules of a first type are attached to said reaction region.

19. A carrier according to claim 1 wherein:
i) the carrier is generally planar such that it has a first and second side;
ii) a reaction region is present on both the first and second side; and
iii) molecules of a first type are attached to the reaction region on the first side of the carrier.

20. An encoded carrier comprising:
a code region having a code; and
a reaction region separate from said code region, said reaction region having a variation in its refractive index or dielectric constant in a direction generally parallel to the surface of the reaction region,
wherein probe molecules which are known are attached to said reaction region and said code indicates information about said probe molecules, and
wherein the reaction region comprising a metal/dielectric interface is configured to support surface plasmons and said variation in the refractive index is configured to couple incident radiation to surface plasmons excited by said radiation.

21. A plurality of encoded carriers, wherein each carrier comprises:
a code region having a code; and a reaction region separate from said code region, said reaction region having a variation in its refractive index or dielectric constant in a direction generally parallel to the surface of the reaction region, wherein a single type of probe molecules which are known are attached to said reaction region and said code indicates the type of probe molecules attached to the corresponding reaction region, and wherein the reaction region comprising a metal/dielectric interface is configured to support surface plasmons and said variation in the refractive index is configured to couple incident radiation to surface plasmons excited by said radiation.

22. A plurality of encoded carriers, wherein each carrier comprises:

a code region having a code; and a reaction region separate from said code region, said reaction region having a variation in its refractive index or dielectric constant in a direction generally parallel to the surface of the reaction region, wherein probe molecules which are known are attached to said reaction region, the plurality of carriers having a plurality of different types of known probe molecules, wherein a single type of probe molecule is attached to each carrier and said code indicates the type of probe molecule attached to the corresponding reaction region of a carrier, and wherein the reaction region comprising a metal/dielectric interface is configured to support surface plasmons and said variation in the refractive index is configured to couple incident radiation to surface plasmons excited by said radiation.

* * * * *